(12) United States Patent  (10) Patent No.: US 7,674,631 B2
Pawliszyn  (45) Date of Patent: Mar. 9, 2010

(54) METHOD AND DEVICE FOR SOLID PHASE MICROEXTRACTION AND DESORPTION

(76) Inventor: Janusz B. Pawliszyn, 383 Dunvegan Dr., Waterloo, ON (CA) N2K 1W7

( * ) Notice: Subject to any disclaimer, the term of this patent is extended or adjusted under 35 U.S.C. 154(b) by 1557 days.

(21) Appl. No.: 10/878,936

(22) Filed: Jun. 29, 2004

(65) Prior Publication Data

US 2005/0011831 A1  Jan. 20, 2005

Related U.S. Application Data

(63) Continuation-in-part of application No. 10/229,101, filed on Aug. 28, 2002, now abandoned.

(60) Provisional application No. 60/480,883, filed on Jun. 25, 2003.

(51) Int. Cl.
*G01N 1/10* (2006.01)
(52) U.S. Cl. .......................... 436/178; 436/161; 422/69; 422/70; 422/101
(58) Field of Classification Search .................. 422/69, 422/70, 101; 436/161, 178
See application file for complete search history.

(56) References Cited

U.S. PATENT DOCUMENTS 6,042,787 A * 3/2000 Pawliszyn .................... 422/69
6,929,778 B2 * 8/2005 Nunes et al. .................. 422/61

* cited by examiner

*Primary Examiner*—Jan M Ludlow

(57) ABSTRACT

A device for carrying out solid phase microextraction on-site is a tubular member having one closed end and one open end with an extracting surface within said tubular member. The extracting surface can be an extracting phase coating extending over a zone within the tubular member. The tubular member is mounted in a housing with an airtight cavity. A method of operation of the device is also provided. The solid phase microextraction device facilitates the ultimate goal of chemist to perform analysis on-site at place where a sample is located rather than moving the sample to laboratory, as it is a common practice in many cases at present. This approach eliminates errors and reduces the time associated with sample transport and storage and, therefore, it results in more accurate, precise and faster analytical data.

20 Claims, 22 Drawing Sheets

METHOD AND DEVICE FOR SOLID PHASE MICROEXTRACTION AND DESORPTION

Continuation of U.S. provisional application No. 60/480,883 filed on Jun. 25, 2003 entitled "Time-Weighted Average (TWA) and Field Sampling Devices for Air and Aqueous Environments Based on Coated Fiber-in-Needle Concept" and Continuation-in-part of U.S. patent application No. 20030003596 filed on Aug. 28, 2002 entitled "Method and Device for Solid Phase Microextraction and Desorption".

BACKGROUND OF THE INVENTION

1. Field of Invention

This invention relates to a method and device for solid phase microextraction and analysis and, in particular, relates to microextraction and analysis being carried out using various types of a single fiber or capillary which can be coated with various materials or uncoated.

2. Description of the Prior Art

Presently, in the organic analysis of environmental samples which involve the separation of components of interest from such matrices as soil, water, fly ash, tissue or other material, liquid extraction is traditionally used as the separation process. For example, water samples are usually extracted with organic solvent. Similarly, solid samples are leeched with an organic solvent in a SOXHLET apparatus. Methods based on solvent extraction are often time consuming, difficult to automate and are very expensive since they require high purity organic solvents and these organic solvents are expensive to dispose of. Further, the organic solvents usually have high toxicity and are difficult, to work with. In addition, the extraction processes can be highly non-selective. Therefore, sequential chromatographic techniques must sometimes be used to separate complex mixtures after extraction, significantly increasing the overall analysis time and the cost. EP-A1-159 230 discloses an extraction method of components in a liquid by placing packets of fibers in contact with said liquid in extracting the components.

Solid phase extraction is a known effective alternative to liquid-liquid extraction in the analysis aqueous samples. The primary advantage of-solid phase extraction is the reduced consumption of high purity solvents and the resulting reduction in laboratory costs and the costs of solvent disposal. Solid-phase extraction also reduces the time required to isolate the analyte of interest. However, solid phase extraction continues to use solvents and often suffers from high blank values. Further, there is considerable variation between the products offered by different manufacturers and lot-to-lot variation can be a problem when carrying out solid phase extraction procedures. Solid phase extraction cartridges available for manufacturers are normally constructed of plastic which can adsorb the analyte and increase interferences in the analysis. The disposable plastic cartridges used in the solid phase extraction process are first activated using organic solvent. The excess organic solvent is then removed and the sample to be tested is passed through the cartridge. The organic components from the sample. are adsorbed on the chemically modified silica surface of the material in the cartridge. Both molecules of interest as well as interferences are retained on the cartridge material. During desorption, a selective solvent is chosen to first remove the interferences. The analyte is then washed out of the cartridge. The analytical procedure from that point is identical to that used in liquid-liquid extraction. The analyte is first preconcentrated and the mixture is then injected into an appropriate high resolution chromatographic instrument. Steps involving the use of organic solvents are the most time consuming.

SUMMARY OF THE INVENTION

A device for carrying out solid phase microextraction of components contained in a fluid carrier is characterized by, in combination, a fiber and a housing surrounding said fiber, said housing containing access means so that said carrier and components could be brought into contact with said fiber.

A method of carrying out solid phase microextraction and analysis with components contained in a carrier uses a fiber. The method is characterized by placing said fiber in contact with said carrier containing said components for a sufficient period of time for chemical extraction to occur, subsequently removing said fiber from said carrier and placing the fiber into a suitable analytical instrument and carrying out desorption with respect to at least one component on said fiber.

A method of carrying out solid phase microextraction and analysis with components contained in a carrier uses a fiber contained in a housing. The housing has access means so that said carrier can be brought into contact with said fiber. The method is characterized by contacting said fiber with said housing for a sufficient time to allow chemical extraction to occur, ending said contact and placing said fiber in a suitable analytical instrument in such a manner that desorption occurs with respect to at least one component on said fiber.

A device for carrying out solid phase microextraction of components contained in a fluid carrier has a tubular member having one closed end and one open end. There is a zone within said tubular member having an extracting surface. The tubular member is located within a housing consisting of supporting element, which surrounds the tubular member, sealing element and plunger. The sealing element is movable along said tubular member and has a cavity. The open end of the tubular member fits into said cavity forming airtight seal, said cavity provides an open position and a closed position for said tubular member. The tubular member is in closed position, when said open end of said tubular member fits into said cavity. When said tubular member is removed from said cavity it is in open position permitting contact between fluid carrier and said zone having extracting surface. The sealing element is removable prior to desorption of extracted components from the extracting surface. The sealing element have openings permitting contact between said fluid carrier and said open end of said tubular member when in said open position. The tubular member being sized and shaped to fit into an injection port of a suitable analysis instrument where said components can be desorbed from said extracting surface A device for carrying out solid phase microextraction of components contained in a fluid carrier has a tubular member having one closed end and one open end. The tubular member consists of a fiber inside a capillary. Said fiber is movable within said capillary. A zone of extracting surface is located on said fiber. Outside diameter of a portion of said fiber is made to mach the inner diameter of said capillary. Said portion of said fiber is located between the closed end of said tubular member and said zone. Movement of said fiber within said capillary allows drawing or expelling said carrier fluid. Optionally said portion of said fiber can be made by o-ring forming piston, which can draw or expel said carrier fluid.

A device for carrying out solid phase microextraction of components contained in a fluid carrier has a tubular member having one closed end and one open end. The tubular member is a capillary, which has a zone of an extracting surface therein. The extracting surface is located inside said capillary. The capillary have a hole in its sidewall in-between said zone and said closed end. The capillary is surrounded by the slidable supporting element, containing a tubular channel, which tightly fits around the capillary. The supporting element provides a sealed position for said hole when said supporting element covers the area of the capillary containing said hole and open position, when it is removed. When the opening of the needle is in contact with fluid carrier the supporting element is in sealed position and open position during desorption of said components into analytical instrument allowing desorption fluid to enter through the hole and flow through said tubular member.

A method of using a device for solid phase microextraction of components from fluid carrier, said device having a tubular member having one closed end and one open end, a zone within said tubular member having an extracting surface, said tubular member being located within a housing, said housing having movable sealing element, said sealing element having a cavity to which said open end of said tubular member fits forming airtight seal, said sealing element being movable, said cavity providing an open position and a closed position for said tubular member, said method comprising exposing the device to the fluid carrier, placing the sealing element in said open position permitting contact between said fluid carrier and said open end, placing said sealing element in a closed position, removing said sealing element, inserting said tubular member into an injection port of a suitable analysis instrument and desorbing said components from said extracting surface.

A method for carrying out solid phase microextraction of components contained in a fluid carrier using a tubular member having an open end and a closed end, said tubular member consisting of a fiber in a capillary, a zone of said fiber having a surface with an extracting phase coating thereon, the outside diameter of a portion length of said fiber is made to be the same as the inner diameter of said capillary, said portion being located in-between the closed end of said tubular member and said zone said method comprising moving said fiber within said tubular member allowing drawing or expelling said carrier fluid.

A method for carrying out solid phase microextraction of components contained in a fluid carrier using a tubular member having an open end and a closed end, a zone of said tubular member near said open end having an extracting surface located therein, said tubular member having a hole in said tubular member wall in-between said zone and said closed end said tubular member being surrounded by the movable supporting element, containing a tubular channel, which tightly fits around said tubular member said supporting element providing a sealed position for said hole when said supporting element covers the area of the tubular member containing said side hole and open position, when it is removed from area containing said side hole, said method comprising of inserting said tubular member into an inlet to analysis instrument in a manner that places side hole in said open position and forms restriction seals around said open end of said tubular member and inlet liner, thereby forcing the flow of desorption fluid through said tubular member.

A method including the steps of removing said sealing element and immediately placing the tubular member into a sealed housing said housing being a multiple tubular member holder, transporting the housing to a suitable analysis instrument, removing said tubular member from said housing and desorbing said components into said instrument.

A method wherein said analytical instrument is automated, said method including the steps of automatically removing a tubular member from said multiple tubular member holder and placing said tubular member into the injection port of an analytical instrument and automatically carrying out desorption.

BRIEF DESCRIPTION OF THE DRAWINGS

FIG. 7b shows a chromatogram produced when using the prior art method of liquid-liquid extraction for the same components as those of FIG. 7a;

DESCRIPTION OF A PREFERRED EMBODIMENT

Figure 1:
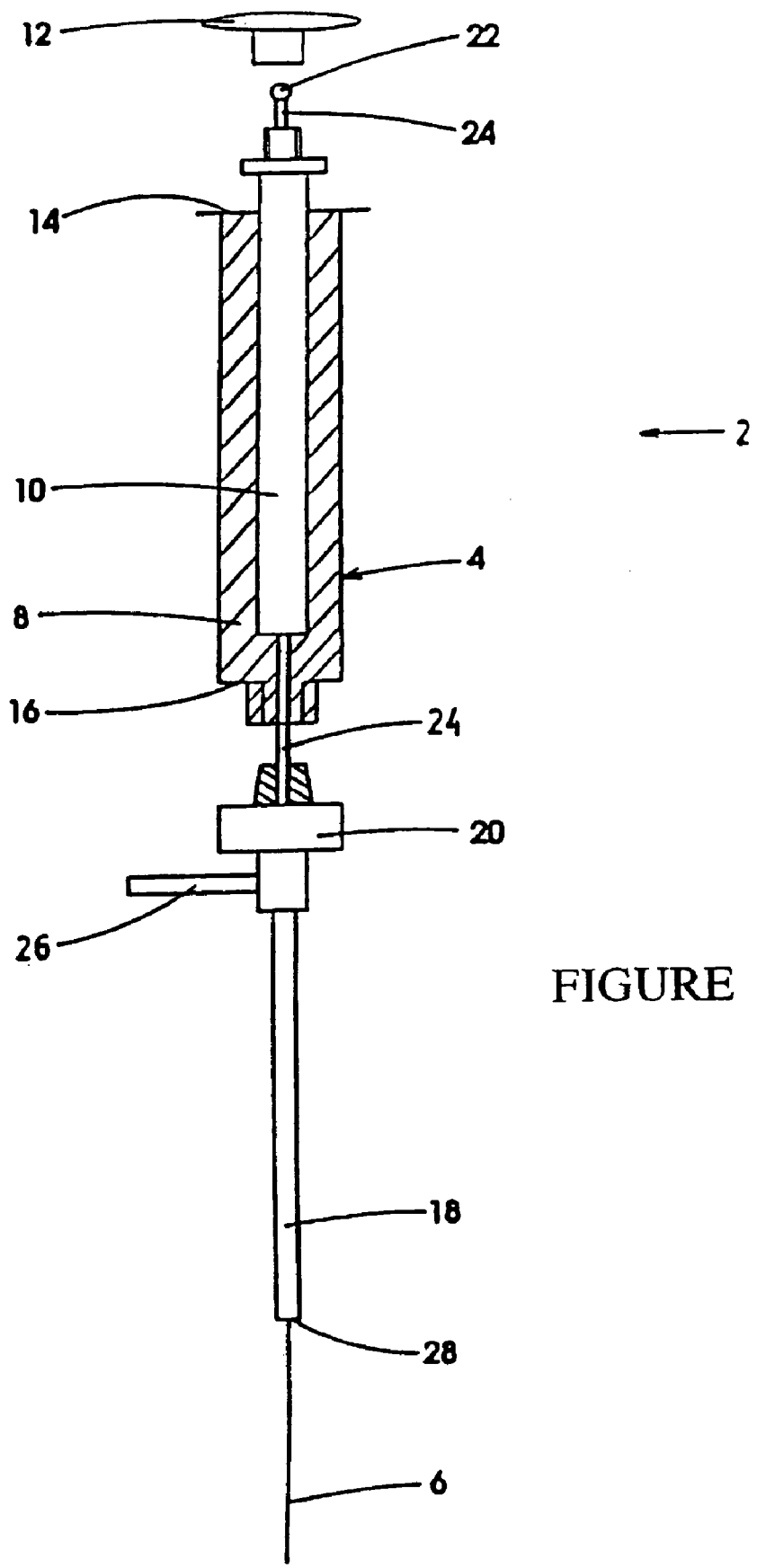
FIG. 1 is a partial sectional side view of a syringe and fiber with the plunger depressed.
Figure 2:
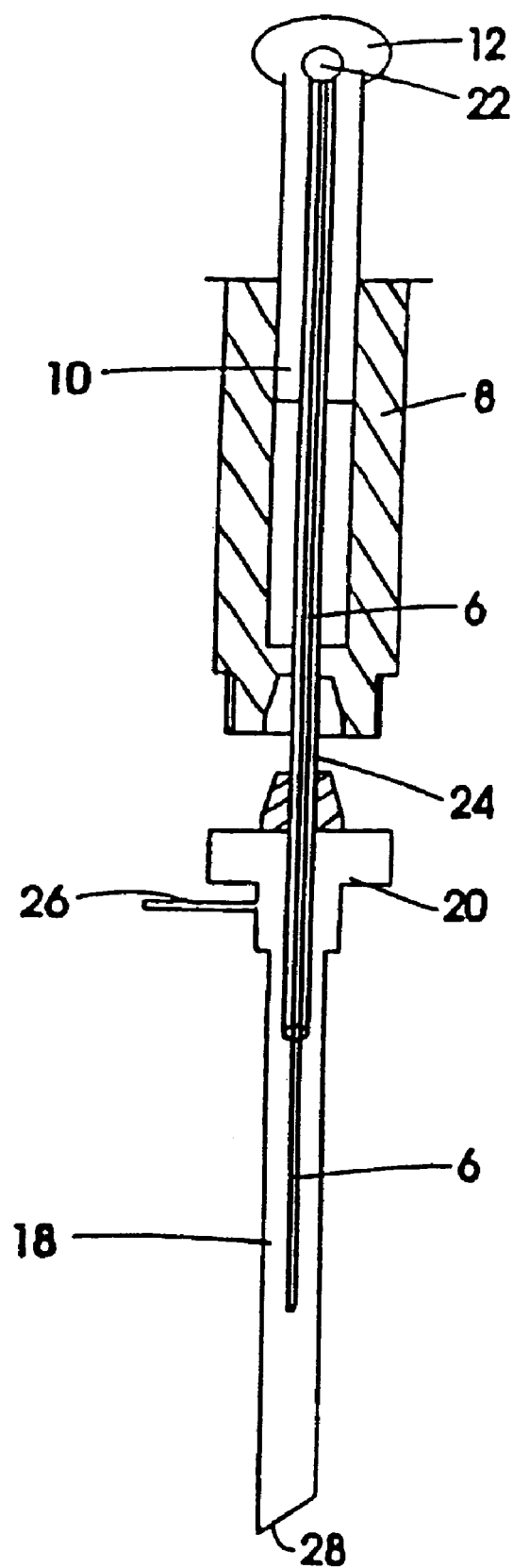
FIG. 2 is a schematic side view of a slightly different syringe and fiber with the plunger withdrawn.

Referring to FIGS. 1 and 2 in greater detail, a device 2 for carrying out solid phase microextraction has a syringe 4 containing a fiber 6. The syringe 4 is made up of a barrel 8 which contains a plunger 10 and is slidable within the barrel 8. The plunger 10 has a handle 12 extending from one end 14 of the barrel 8. At the opposite end 16 of the barrel 8, there is located a needle 18 which is connected to the end 16 by the connector 20. The handle 12 and the needle 18 and connector 20 are shown in an exploded position relative to the barrel 8 for ease of illustration.

The fiber 6 is a solid thread-like material that extends from the needle 18 through the barrel 8 and out the end 14. An end of the fiber 6 (not shown) located adjacent to the cap 12 has retention means 22 located thereon so that the fiber will move longitudinally as the plunger 10 slides within the barrel 8. The retention means can be simply a drop of epoxy which is placed on the end of the fiber 6 near the handle 8 and allowed to harden. The fiber 6 is partially enclosed in a metal sleeve 24 which surrounds that portion of the fiber 6 located within the plunger 10, the barrel 8 and part of the needle 18. The purpose of the metal sleeve 24 is to protect the fiber 6 from damage and to ensure a good seal during operation of the device. Extending from the connector 20 is an optional inlet 26. The purpose of the inlet 26 is to allow alternate access to the fiber. For example, when the fiber is contained within the needle 18, fluid could contact the fiber 6 by entering the inlet 26 and exiting from a free end 28 of the needle 18. The inlet 26 can also be used to contact the fiber with an activating solvent.

In FIG. 2, a schematic version of the device 2 is shown. The plunger is in a withdrawn position and the free end of the fiber 6 is located entirely within the needle 18. The access permitted by the inlet 26 when the fiber is in the position shown in FIG. 2 can readily be understood. Obviously, fluid contacting the fiber 6 within the needle 18 could also enter the free end 28 of the needle 18 and exit from the access 26.

Figure 3:
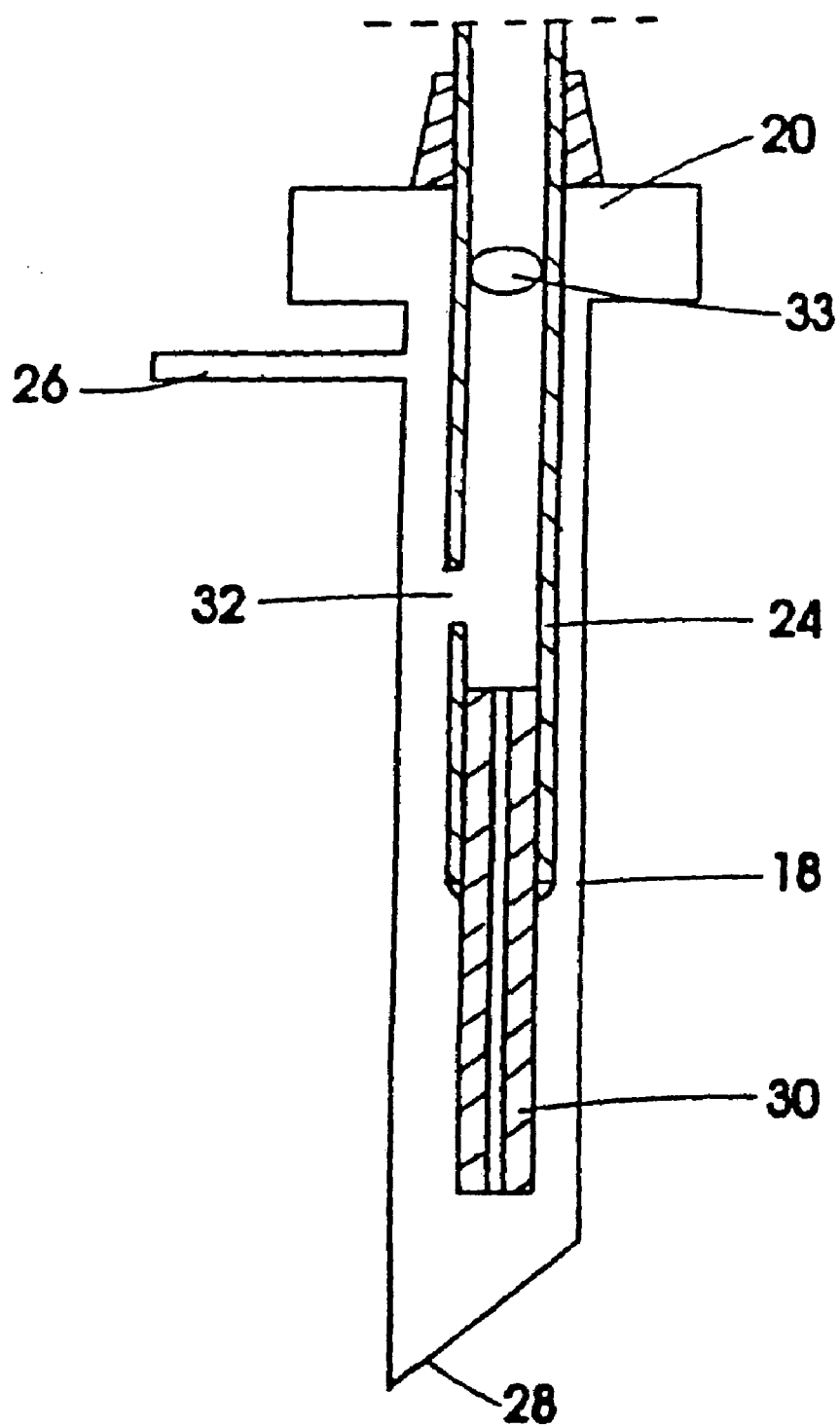
FIG. 3 is a schematic side view of a needle portion of a syringe containing a hollow fiber.

In FIG. 3, only the needle portion of the device is shown. A fiber 30 extending from the metal sleeve 24 is hollow. It can be seen that there is an opening 32 in the wall of the metal sleeve 24 to allow access to an interior of the sleeve 24 as well as an interior of the fiber 30. For example, fluid could enter the inlet 26 and an interior of the needle 18. Then, the fluid could pass through the opening 32 and through an interior of the fiber 30 and ultimately exit from the free end 28 of the needle 18. In this embodiment, the fiber does not extend to the handle 12 (not shown) but only the metal sleeve 24 extends to the handle 12. The fiber 30 can still be moved beyond the end 28 of the needle 18 by depressing the plunger and returned to the position shown in FIG. 3 by moving the plunger to the withdrawn position.

Alternatively, if it is desired to have the fiber 30 located within the needle 18 at all times, contact with the fiber 30 can be attained through the inlet 26 or the opening 32 and the free end 28. A plug 33 located within the metal sleeve 24 prevents any fluid from travelling up the sleeve to the handle. In some situations, the fluid could flow through the sleeve 24.

In general terms, the syringe could be said to be a housing for the fibers 6, 30 and the access means could be the action of the plunger 10 in moving the fiber beyond the end 28 or, alternatively, the access means could be the inlet 26.

The disadvantages and inconveniences of the previous processes for analyzing various fluids are overcome by the solid phase microextraction technique of the present invention. The diameter of the fibers will vary but will preferably be between 0.05 millimeters and 1 millimeter. Much of the experimentation on which the present invention was based, was carried out using fused silica fibers that were chemically modified. The fused silica fibers are widely used in optical communication and are often referred to as optical fibers.

Chemical modification of these fibers can be achieved by the preparation of the surface involving etching procedures to increase the surface area followed by chemical attachment of the desired coating. The stationary phases bonded to the surface of the silica fibers are similar to that used in fused silica gas chromatograph columns or high performance liquid chromatography columns.

As an example, fused silica fibers were obtained from Polymicro Technologies Inc., Phoenix, Ariz. and these fibers were coated with polyimide and had an outer diameter of approximately 171 µm. Uncoated fused silica was obtained by burning off the polyimide coating and gently scraping off the charred portion. To use the polyimide film as a stationary phase, it was first heated at 350° C. for four hours. The polyimide was then burned off and the char removed, except for a one to two millimeter portion at the end of the fiber. In all cases, the polyimide was burned off after the fiber had been inserted into the syringe and trimmed to the correct length. After burning, the fiber became fragile and had to be handled carefully. The metal casing is used to strengthen the fiber. The normal lifetime for a prepared fiber was five to six weeks with regular use.

The solid phase microextraction process does not require a sophisticated coating system to be a useful technique. Either the uncoated fiber, fused silica, silicone or the polyimide films that optical fibers are shipped with can be a suitable stationary phase.

The method of solid phase microextraction and analysis consists of a few simple steps. For example, when a water matrix sample containing components of interest is desired to be analyzed, the plunger of the syringe is depressed and the exposed fiber extending from the free end of the needle is inserted into the water matrix sample. The organic components of the water are extracted into the non-polar phase. Water is considered to be the carrier in a water matrix sample. Where the water sample is contained in a bottle containing a septum, the needle is inserted through the septum first before the plunger is depressed so that the fiber will not be damaged by the septum. When the microextraction has occurred to a sufficient degree (usually approximately two minutes), the plunger is moved to the withdrawn position causing the fiber to be drawn into the needle and the needle is removed from the sample bottle through the septum. Preferably, the sample is stirred while the fiber is inserted. The time for extraction will depend on many factors including the components being extracted as well as the thickness and type of coating, if any, on the fiber. Usually, the extraction time is approximately two minutes. The plunger is then moved to the withdrawn position to retract the fiber into the needle. The needle is then removed from the bottle and is inserted through the septum in an injection port of a conventional gas chromatograph or other suitable analytical instrument. The plunger is then depressed again to expose the fiber and the organic analytes on the fiber are thermally desorbed and analyzed. The fiber remains in the analytical instrument during the analysis. When the analysis has been completed, the plunger is moved to the withdrawn position and the syringe is removed from the injection port.

Various injection ports are suitable such as the "split-splitless" type or the "on-column" type.

While various types of syringes will be suitable, a HAMILTON 7000 (a trade mark) series syringe has been found to be suitable. The syringe facilitates convenient operation of the solid phase microextraction process and protects the fiber from damage during the introduction into a sample bottle or into an injector of an analytical instrument or even during storage. The length of the fiber depends on the injector of the analytical instrument with which the fiber will be used. Preferably, the fiber is mounted in a housing to a movable part so that the fiber is movable longitudinally within the housing. Still more preferably, the movable part moves a sufficient distance so that at least part of said fiber can be extended outside of said housing and retracted into said housing successively. The movable part is preferably an elongated member which extends partially outside of the housing. The part of the elongated member that extends partially outside of the housing preferably has a handle thereon. The elongated member can be a plunger.

In addition to the improved convenience of the present device and method, the method differs significantly in the extraction part of the process compared to the prior art solid phase extraction process using cartridges. The extraction process in accordance with the present invention does not require prior sampling of aqueous material since in-vivo or in-vitro sampling can be conveniently performed. The microextractor can be directly inserted into the fluid stream. The simple geometry of the fiber eliminates clogging caused by particle matter present in the samples. Also, due to the small size of the fiber, not all of the organic compounds are extracted but rather the equilibrium described by the partition coefficient between the water and organic stationary phase for a given analyte is established. Therefore, the solid phase microextraction method of the present invention can be made selective by appropriate choice of a specifically designed organic phase. The partitioning between the aqueous phase and the organic coating can be described through the distribution constant, K:

$$K = \frac{C_s}{C_{aq}} \quad (1)$$

where $C_s$ is the concentration in the stationary phase and $C_{aq}$ is the concentration in the water. The partition ratio, k', is therefore:

$$k' = \frac{C_s V_s}{C_{aq} V_{aq}} = \frac{n_s}{n_{aq}} = K \frac{V_s}{V_{aq}} \quad (2)$$

where $n_s$ and $n_{aq}$ are the number of moles in the stationary and aqueous phases, respectively, and $V_s$ and $V_{aq}$ are the volumes of the respective phases.

Rearranging Eqn. 2 yields:

$$n_s = K \frac{V_s n_{aq}}{V_{aq}} \quad (3)$$

substituting $C_{aq} V_{aq}$ for $n_{aq}$ results in:

$$n_s = K V_s C_{aq} = A C_{aq} \quad (4)$$

where $A = K V_s$.

A linear relationship between concentration of analytes in aqueous samples and detector response is expected based upon the relationship in equation (4). The slope of the linearity curve can be used to determine the partition coefficient for a given analyte if the volume of the stationary phase is known. Furthermore, the sensitivity of the fiber can be adjusted by changing the volume (thickness or area) of the stationary phase.

The linear dynamic range of the method typically extends several orders of magnitude for coatings similar to chromatographic stationary phase materials. The limit of quantization depends on the partition coefficient and the thickness of the coating and can be as low as a few ppT (parts per trillion), which was obtained for chlorinated solvents. In this case the amount of the solvents extracted by a thick polyimide coating from a water sample is about 30 pg per component at a 1 µg/L concentration. This amount ensures not only ECD detection but will allow mass spectrometric identification and quantization.

Figure 4:
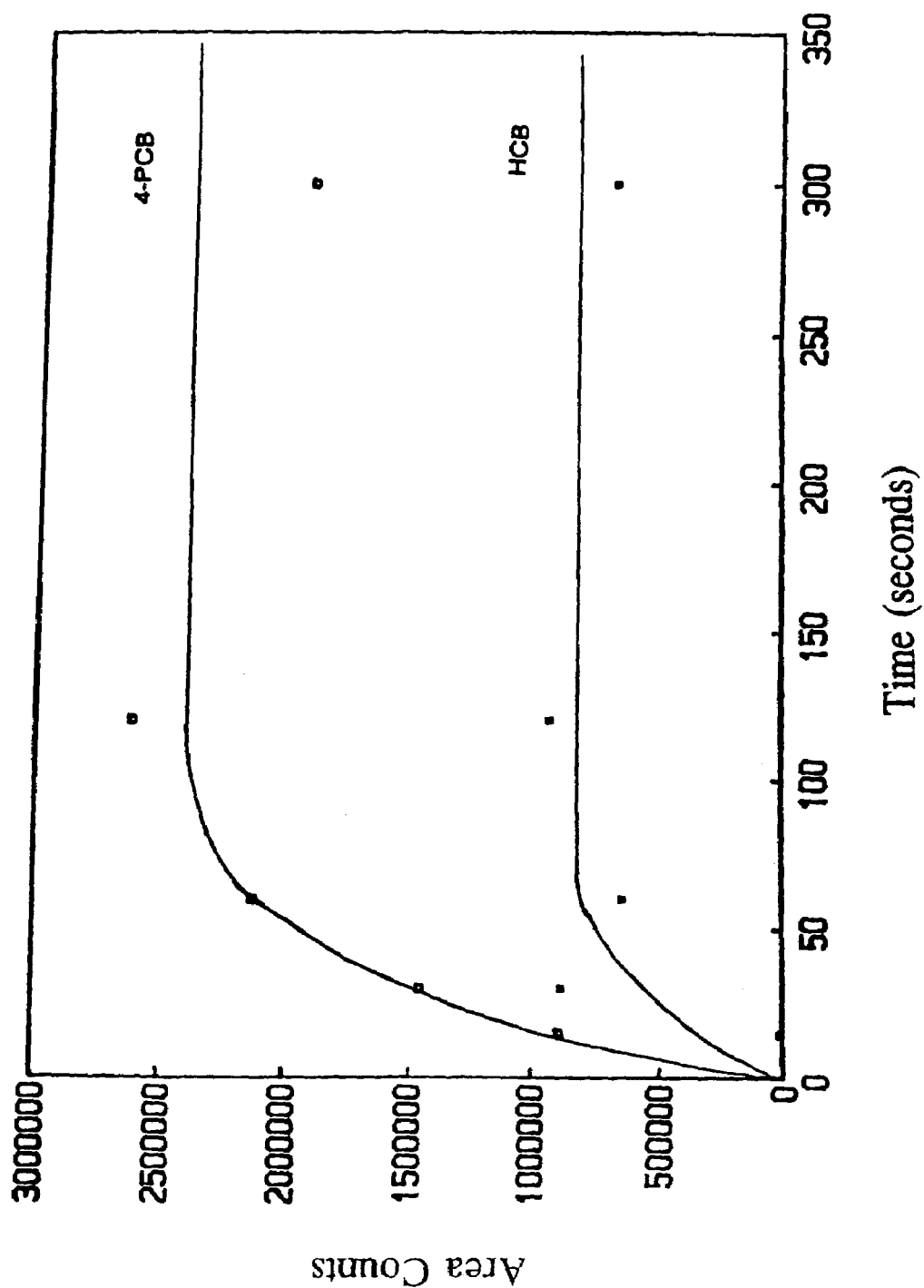
FIG. 4 is a graph of amount of analyte extracted versus time.

The dynamics of the extraction process is illustrated on FIG. 4 which shows an example of a typical relationship between the amount of analyte adsorbed onto the microextractor (peak area) versus the extraction time, which corresponds to the exposure time of the fiber to the water matrix sample. Initially, the amount of analyte adsorbed by the stationary phase increases with the increase in extraction time. This trend is continued until the point of steady state is achieved which causes the relationship to level off. This situation indicates the state of equilibrium between the concentration of the analyte in the stationary phase and in the water matrix sample and defines optimum extraction time. According to FIG. 4, optimum extraction time for uncoated fiber (about 0.1 µm film of silica gel) and PCBs as analytes is about one minute.

Figure 5:
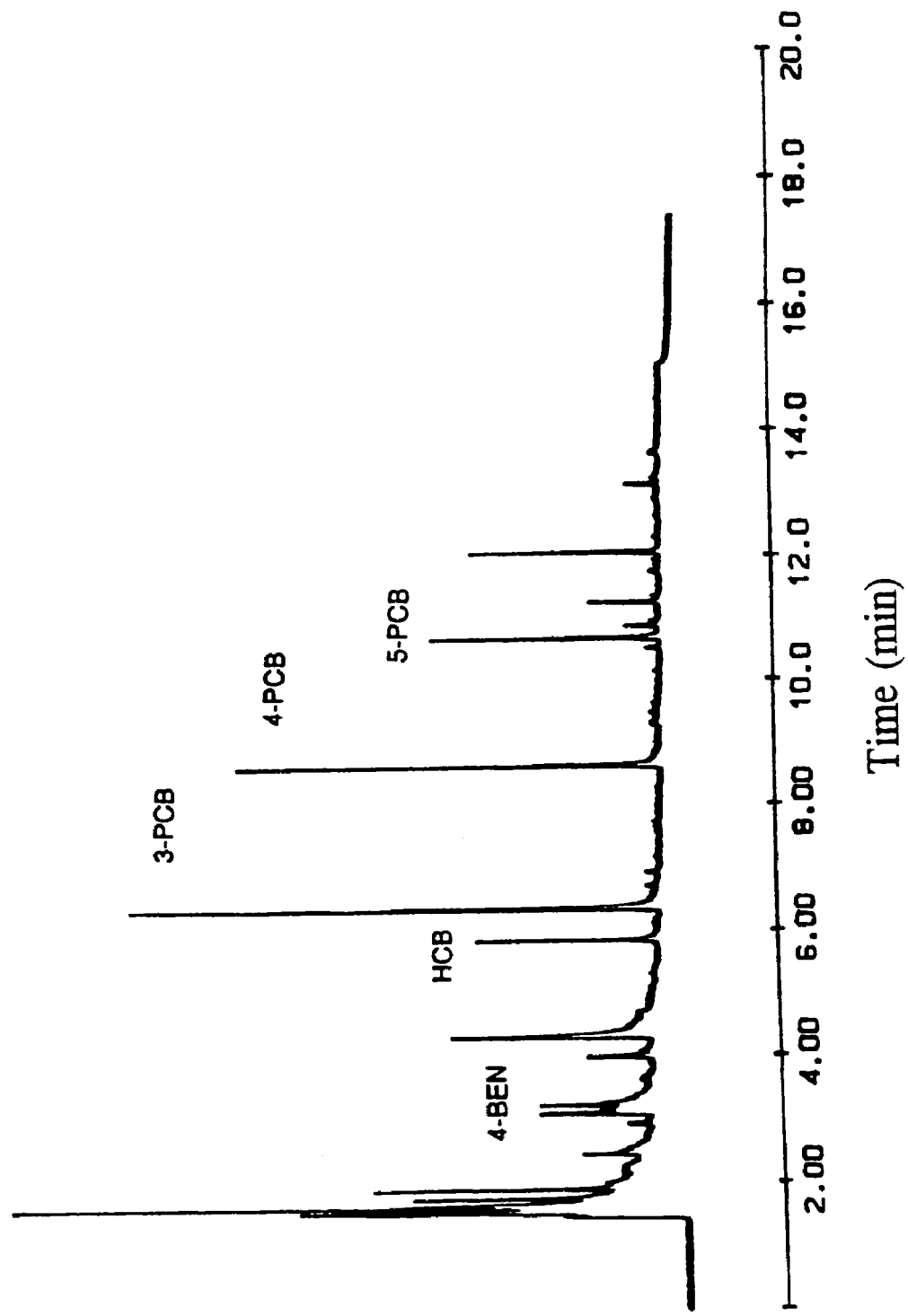
FIG. 5 is a graph showing the results of a typical gas chromatography analysis.

FIG. 5 illustrates the chromatogram corresponding to a PCB mixture in water extracted and analyzed by the solid phase microextraction method. Peak tailing is larger for the more volatile compounds than the heavier, later eluting components. This is an effect of thermal focussing that occurs when the analytes are volatilized at 300° C. and transferred to a 150° C. oven. The heavier compounds benefit from thermal focussing, but the oven is at too high a temperature to allow focusing of the more volatile compounds. The tailing can be alleviated by using a cryogenically cooled oven to improve focusing.

Figure 6:
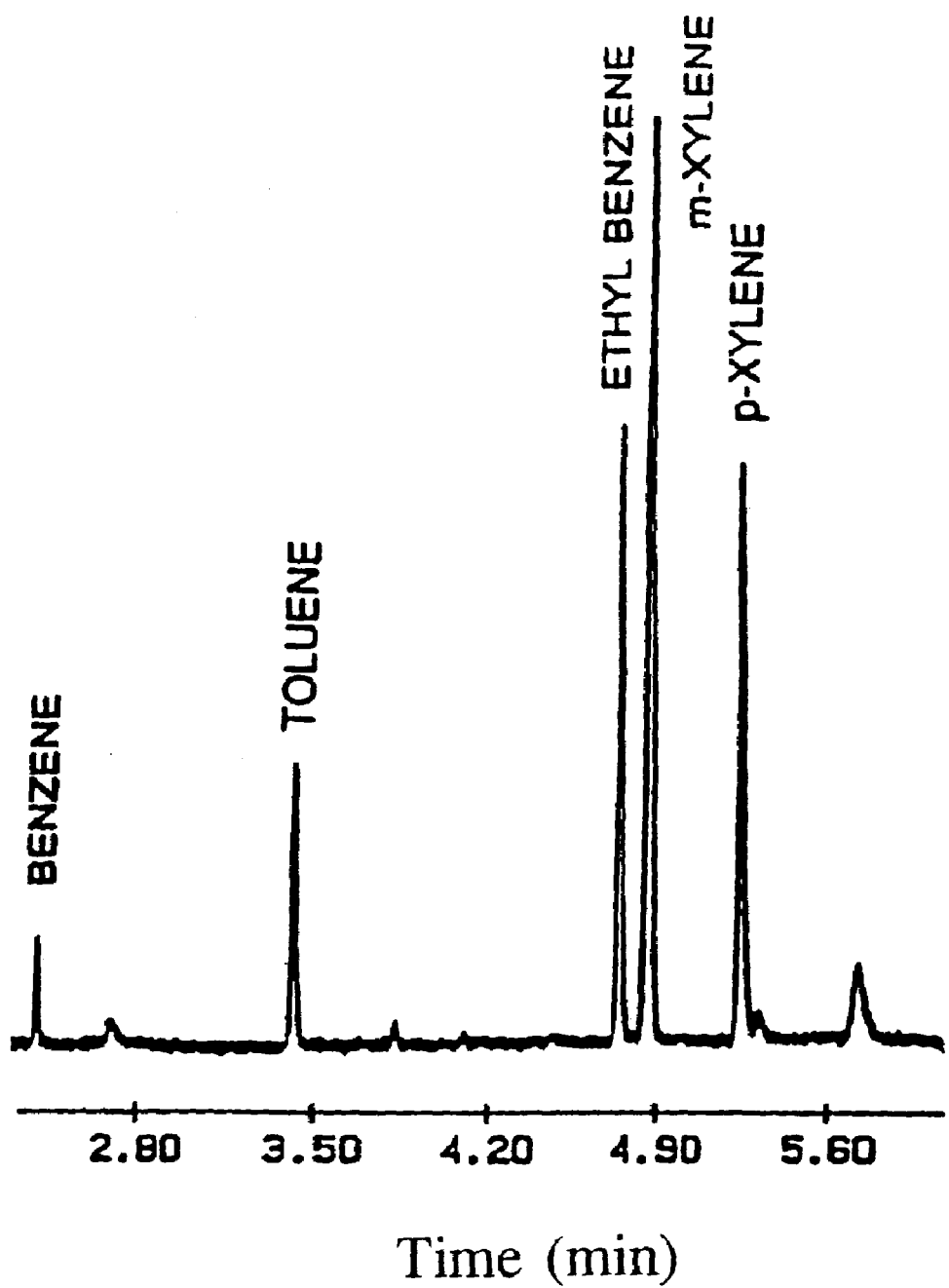
FIG. 6 is a graph showing another analysis from a gas chromatograph.

An uncoated fiber can also be used to adsorb benzene, toluene, ethyl benzene and xylenes (BTEX) from aqueous solutions. For this separation (FIG. 6), a flame ionization detector (FID) was used, illustrating that a sufficient quantity was adsorbed for FID detection. This expands the general applicability of the fiber as FID detectors are somewhat easier to operate and maintain than ECD detectors. The extraction efficiency in this case is sufficiently high to deplete significantly the analyte after 2 to 3 injections if a small volume of aqueous material (1 to 2 mL) is sampled. A larger sample volume (100 mL) is thus recommended if multiple injections are necessary.

Moderate levels of organic interferences and variation in ionic strength of aqueous solution do not significantly change the extraction equilibria. However, large amounts of organic solvent could be added intentionally to introduce partitioning selectivity, as is commonly done in liquid chromatography.

The fiber method has great potential for the analysis of highly sorptive compounds that can be difficult to sample without loss of analyte. Losses to storage bottles and transfer lines could potentially be eliminated by sampling in situ and analyzing the fiber in the field using portable gas chromatograph instrumentation. The device and method of the present invention can utilize a mechanical device such as an autosampler. The autosampler can be programmed to operate the plunger at the appropriate time to contact the carrier and to insert the syringe and the fiber into the injection port of the analytical instrument. The autosampler has an advantage over manual extraction and analysis in that the contact time and the length of the fiber in the carrier as well as in the instrument can be maintained constant. A VARIAN 3500 gas chromatograph and a VARIAN 8100 autosampler has been found to be suitable.

Possible applications of this technique include sampling of both surface and groundwater samples, either in situ or in the laboratory. It could potentially be used in on-line process applications or clinical analysis. Both of these applications benefit from the simplified sample preparation. The coating can be designed for either a broad scan of the organic contaminants (non-selective fiber coating) or selective sampling. This method, when combined with laser desorption, could reduce the sample extraction and analysis to a fraction of a minute. In this technique the optical fiber is used as alight guide. In a variation of the invention, the syringe could have a laser source affixed thereto with activation means and coupling optics to focus light onto the fiber which will transmit the light to a free end thereof to desorb the components thereon. Curie point heating and microwave desorption are alternative desorption methods. The fiber also shows promise as a method of studying the adsorption properties of polymers and for obtaining information about partitioning in liquid chromatographic systems.

Figure 7A:
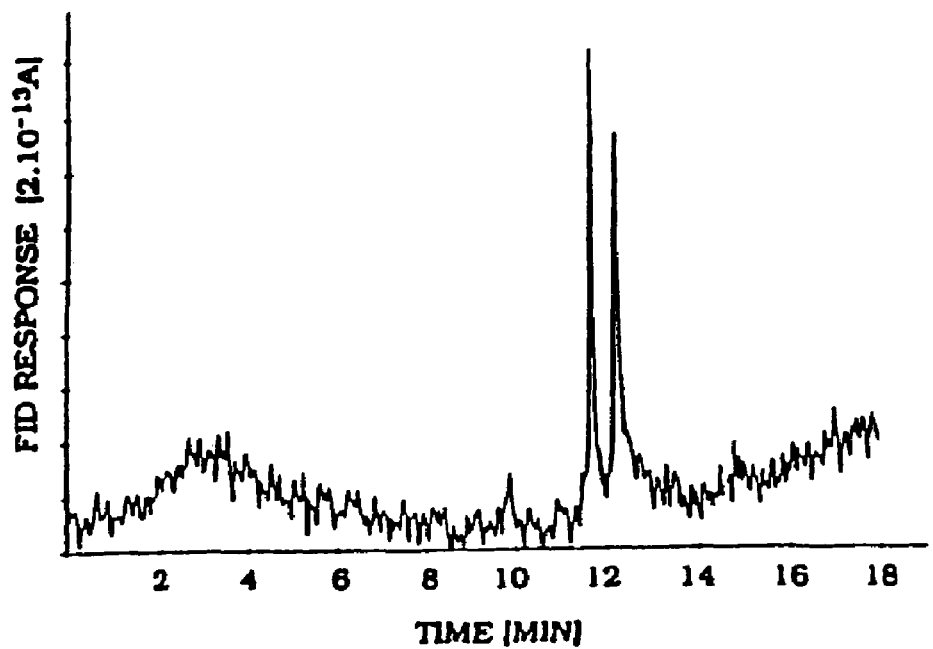
FIG. 7a shows a chromatogram produced when using the solid phase microextraction of the present invention.
Figure 7B:
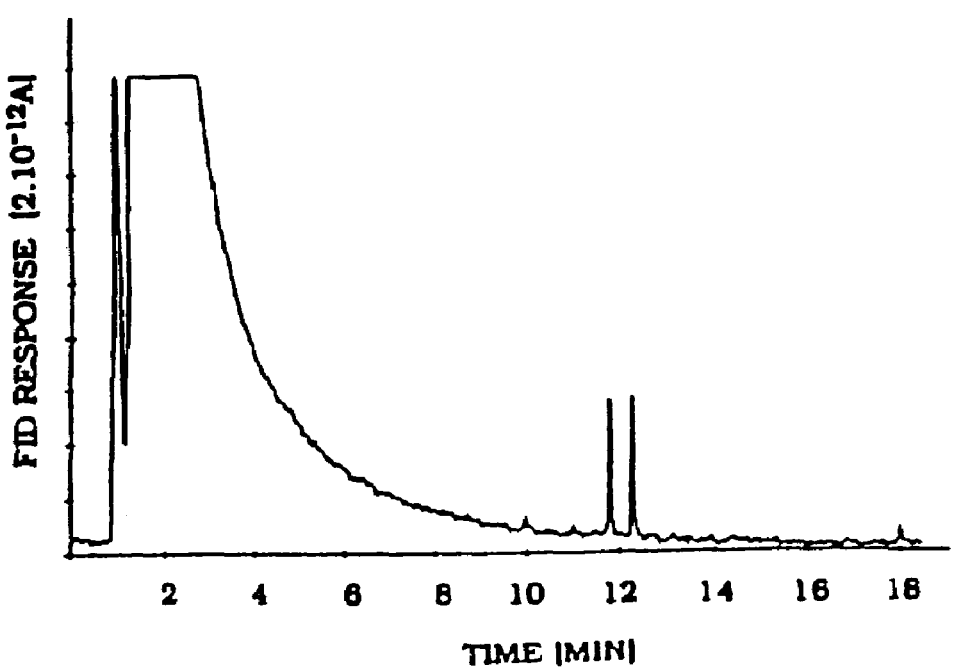

FIG. 7 illustrates the advantages of the method of the present invention compared to the prior art solvent procedure. The chromatogram from FIG. 7a corresponds to silica fiber techniques using C-18 coating and FIG. 7b to liquid-liquid extraction with chloroform. In both cases the same effluent from a sewage treatment plant was analyzed under the same chromatographic conditions. Results are similar, however the total extraction time was about an hour for the solvent method and two minutes for the fused silica fiber technique. The chromatogram for FIG. 7b shows the presence of the solvents used in the liquid-liquid extraction. The solid phase microextraction device facilitates easy sampling in the field. In addition, when organic solvents are used in the preparation step, the corresponding large peak together with possible impurities can mask volatile analytes (FIG. 7b).

Figure 8:
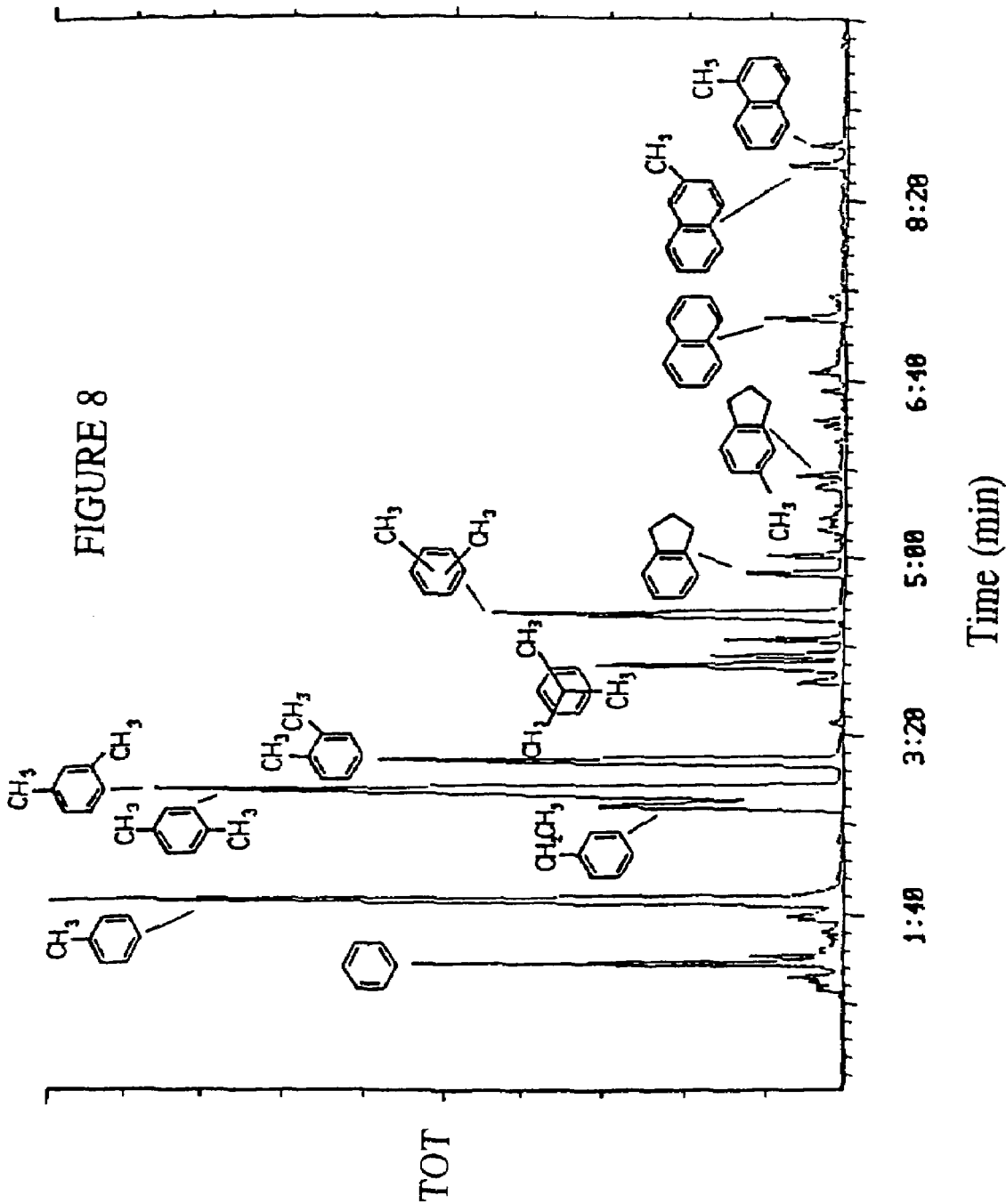
FIG. 8 is a chromatogram of the extraction of gasoline components from water with silicone coated fibers.
Figure 9:
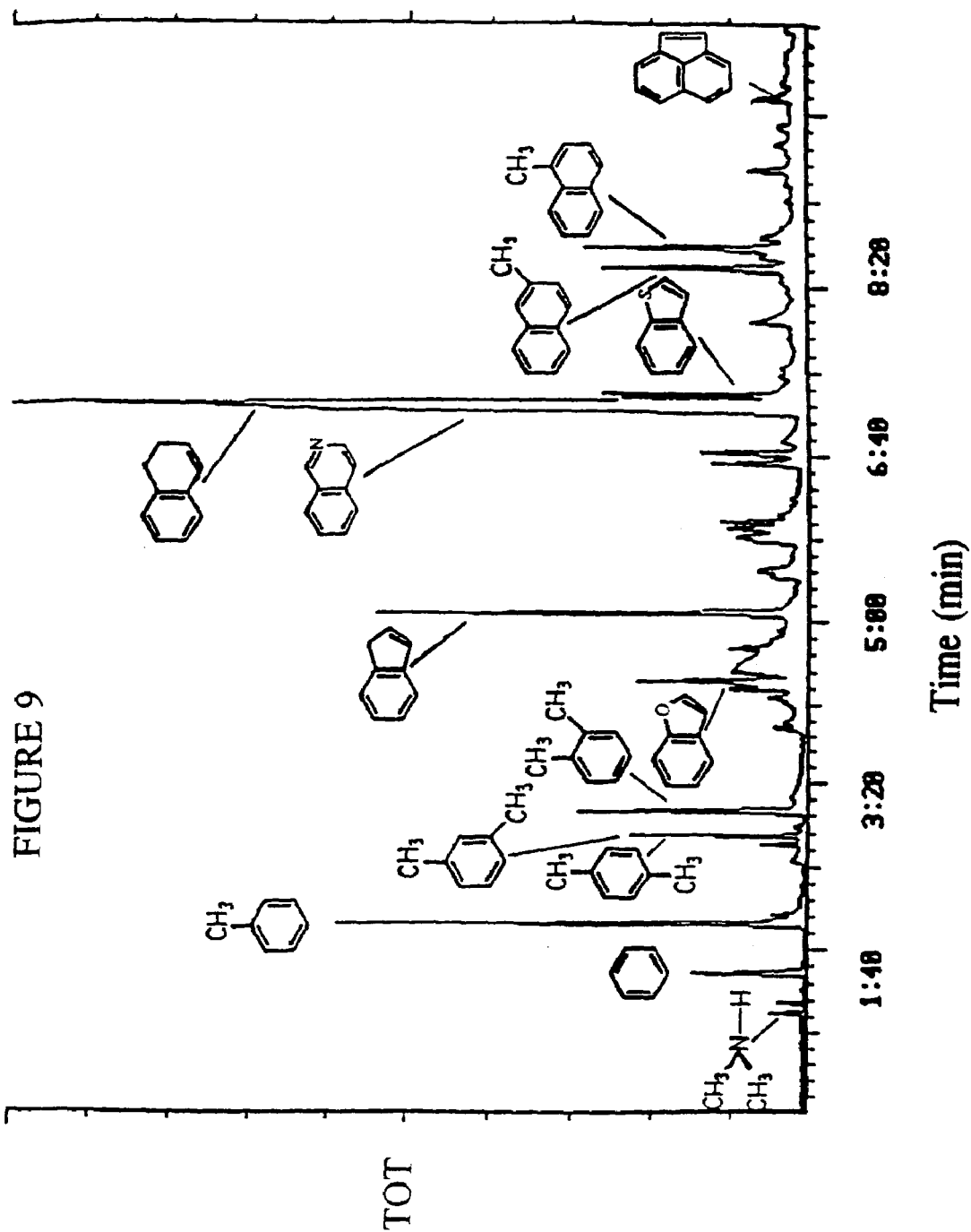
FIG. 9 is a chromatogram from the extraction of organics from coal gasification waste water using a silicone coated fiber.

In FIG. 8, there is shown a chromatograph for the extraction of gasoline components from water using a silicone coated fiber. In FIG. 9, there is shown a chromatograph for the extraction of organics from coal gasification waste water using a silicone coated fiber. Both analyses and identifications for FIGS. 8 and 9 have been done using a mass spectrometry detector.

Figure 10:
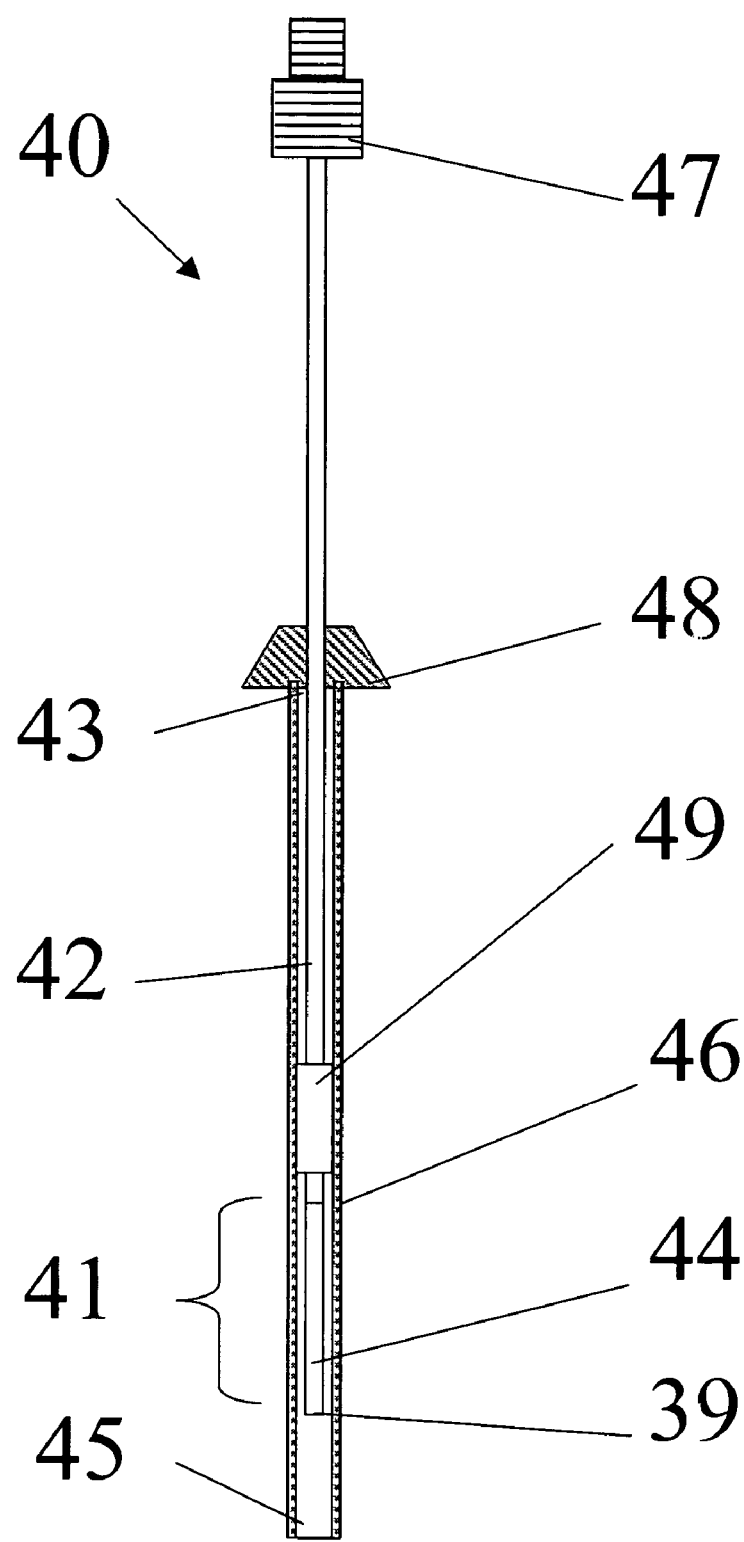
FIG. 10 is a schematic sectional view of a tubular member containing coated fiber with dimensions allowing drawing fluids into the needle.

FIG. 10 illustrates an example of the preferred construction of the tubular member 40 consisting of a fiber 42 in a capillary 46. The fiber 42 and the capillary 46 are made of hard plastic, metal, deactivated stainless steel, alloy or fused silica. The capillary can be a needle. A tubular member 40 has an open end 45 and a closed end 43. Near the open end 45 of the capillary 46 is a zone 41 of a fiber with an extraction phase coating 44. The zone 41 could be located at any position of the fiber 42, but is preferably located near the tip 39 of the fiber 42. Also, the material from which the fiber 42 is formed could be made of a material that would provide an extracting surface without the use of a coating. The capillary 46 is sealed at the closed end 43 with a septa 48. At the opposite end to the coating 44, fiber 42 contains a screw 47, which allows movement of fiber 42 and adjustment of the extraction phase coating position. The fiber 42 can be constructed so that the outside diameter of a portion of said fiber 49 is made to match the inner diameter of said capillary 46. Movement of the fiber up allows drawing fluid to the needle prior to sampling and movement down expels of liquid prior to storage and analysis. This feature is very useful when analyzing liquids using time weighted average (TWA) methods, such as aqueous samples, since the capillary needs to be first flooded with appropriate liquid, for example water, before proper contact with the carrier fluid can be made. Also, the seal provided by the portion of the fiber length 49 is useful to reduce the possibility of analyte loss to the septa 48. Alternatively, a seal can be accomplished by using an o-ring attached onto the fiber. When reference is made to contact between a fluid carrier and the open end of the tubular member or the zone or extracting surface of the tubular member or similar variations thereof, the contact is intended to include and does include contact with a headspace of the fluid carrier.

Figure 11:
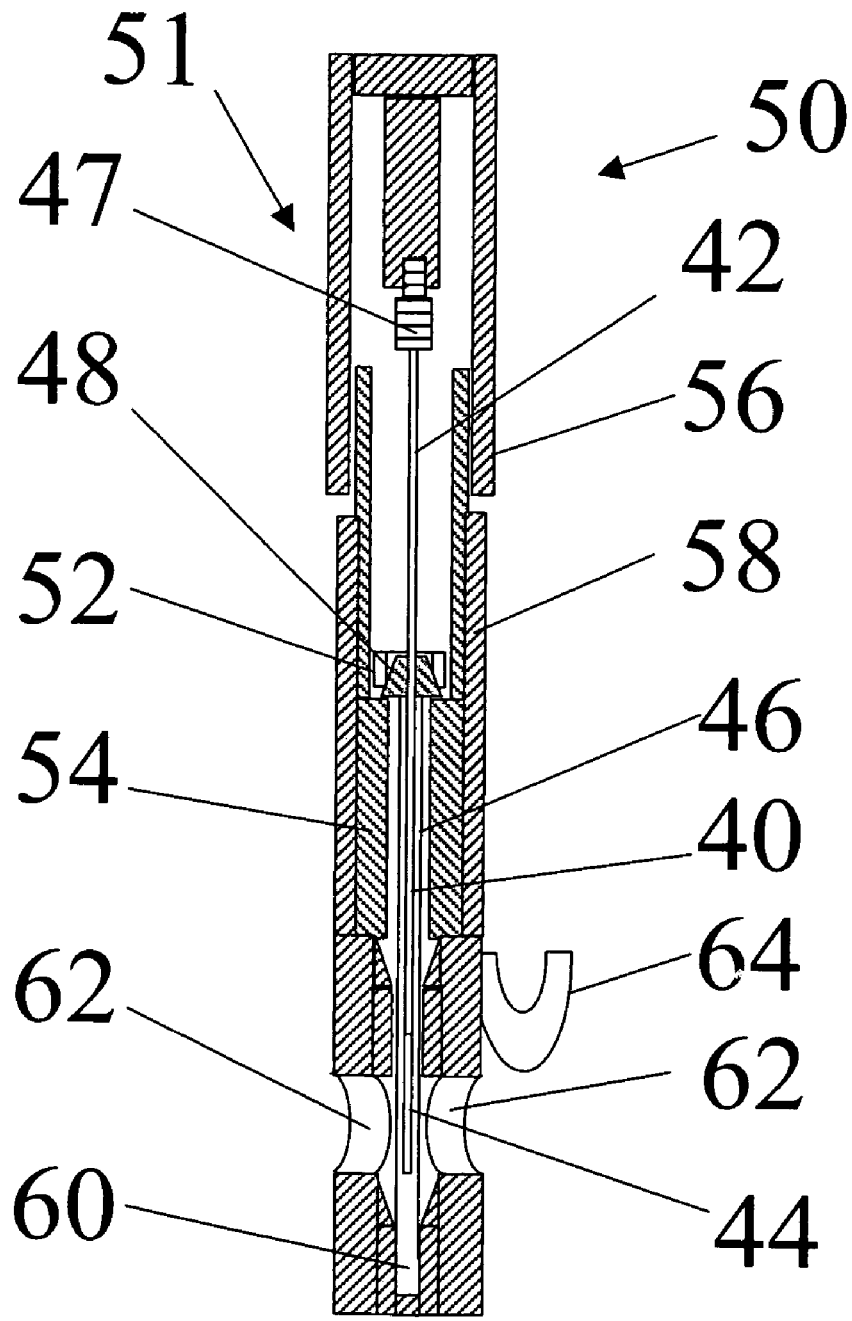
FIG. 11 is a schematic sectional view of a tubular member containing fiber coated by the extraction phase in a protective housing producing airtight cavity at the open end of the tubular member.

In FIG. 11 there is shown the construction of device 50 incorporating tubular member 40 in a housing 51 consisting of sealing element 58, supporting element 54 and plunger 56. The device 50 is designed for on-site implementation, protection against the loss of extracted compounds and for automated introduction to analytical instruments. FIGS. 12, 13, 14, 15 and 16 show the operation of the device for carrying out solid phase microextraction of components contained in a fluid carrier (not shown). FIG. 11 illustrates the device in a closed position. Sealing element 58, which is movable, surrounds the tubular member 40 and supporting element 54 and has a cavity 60. The closed end of the tubular member is attached to the supporting element by using screw 52. A screw 47 is used to attach the fiber to the plunger 56. The cavity 60 in the sealing element 58 provides an open position and a closed position for the tubular member. The tubular member consists of fiber 42 in capillary 46. In the closed position, the open end of the capillary 46 is placed in the cavity 60 of the sealing element 58 forming an airtight seal. The sealing cavity is made of inert soft material such as TEFLON (a trade mark). In the open position, when the sealing element 58 and the cavity 60 are retracted, the open end of the capillary contacts the fluid carrier. The sealing element is removable from the device. The movement of the sealing element can be accomplished by various means including using threads, notches or o-rings. The sealing element is equipped with the openings 62, which facilitate the contact with the fluid carrier when the device is in an open position (see FIGS. 12-14). In FIG. 11, the sampling device 40 is shown to have an optional clip 64, which allows attachment or mounting of the device during sampling.

Figure 12:
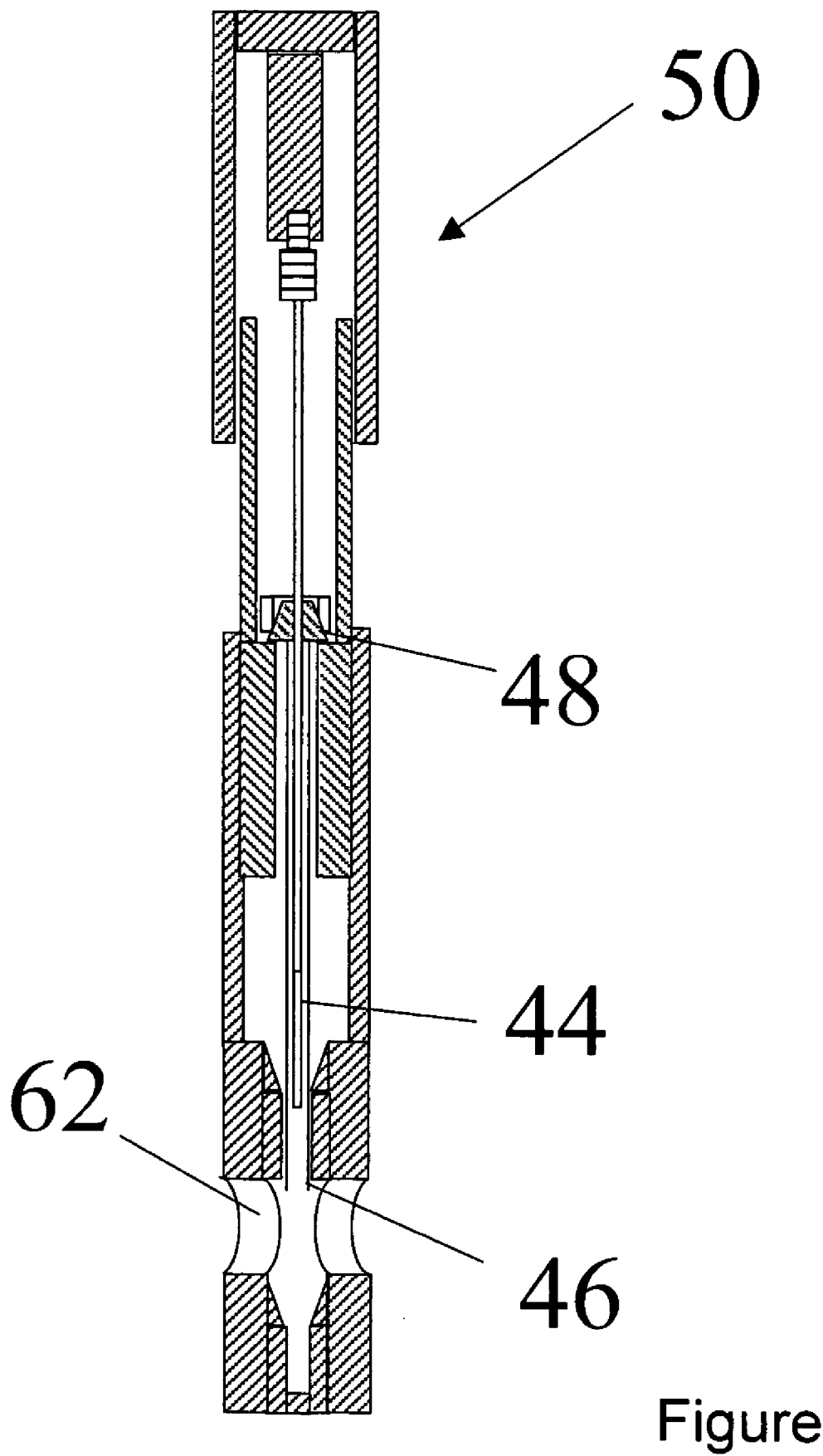
FIG. 12 is a schematic sectional view of a tubular member with coated fiber in a protective housing with open end.
Figure 13:
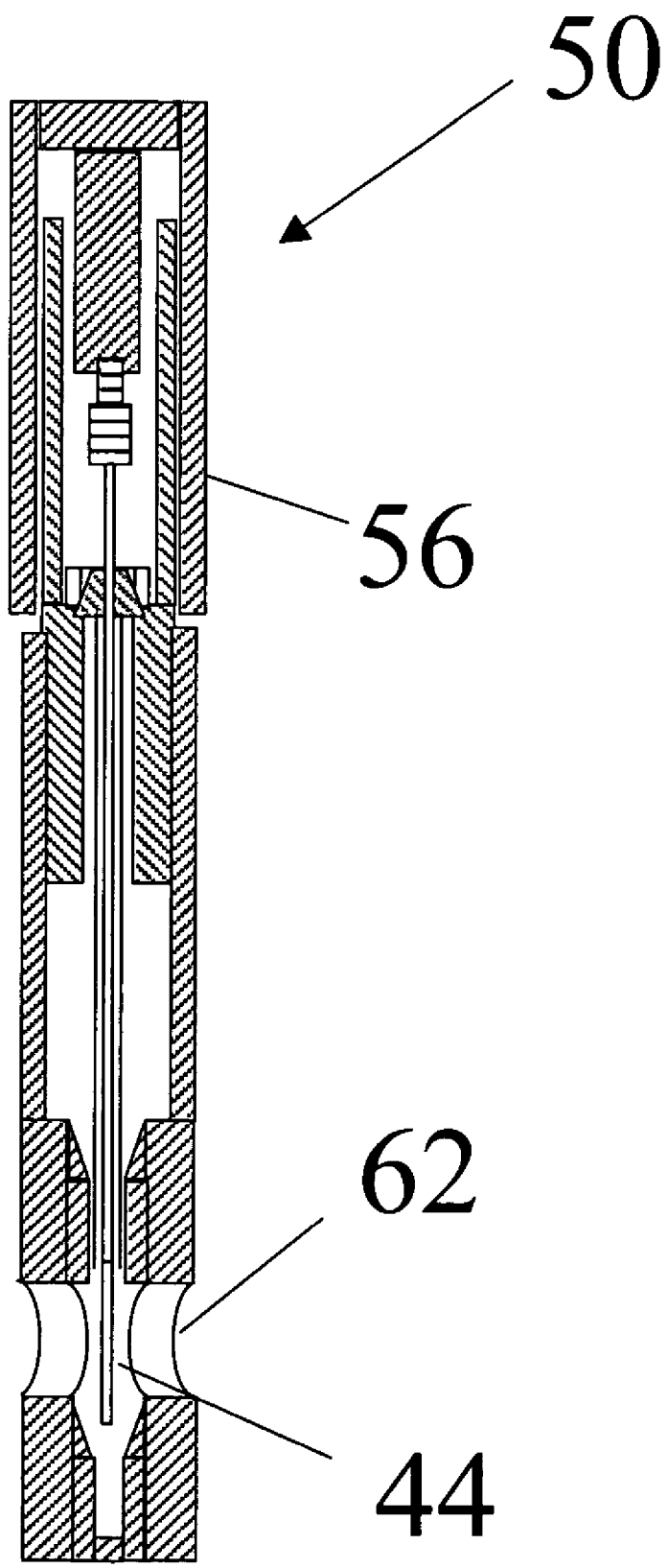
FIG. 13 is a schematic sectional view of a tubular member in a protective housing with coated fiber exposed to the sample via openings in a sealing element.
Figure 14:
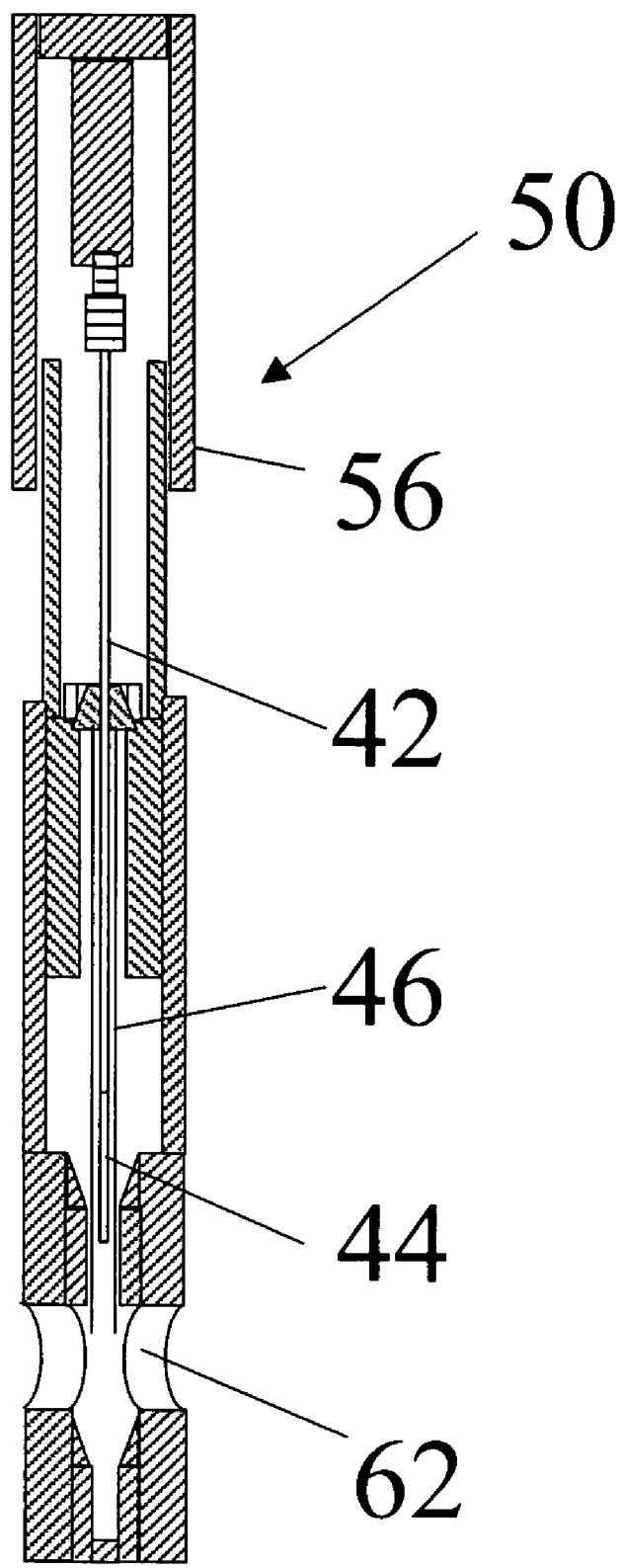
FIG. 14 is a schematic sectional view of a coated fiber in a needle and the protective housing in a position ready to perform time weighted average measurement.
Figure 15:
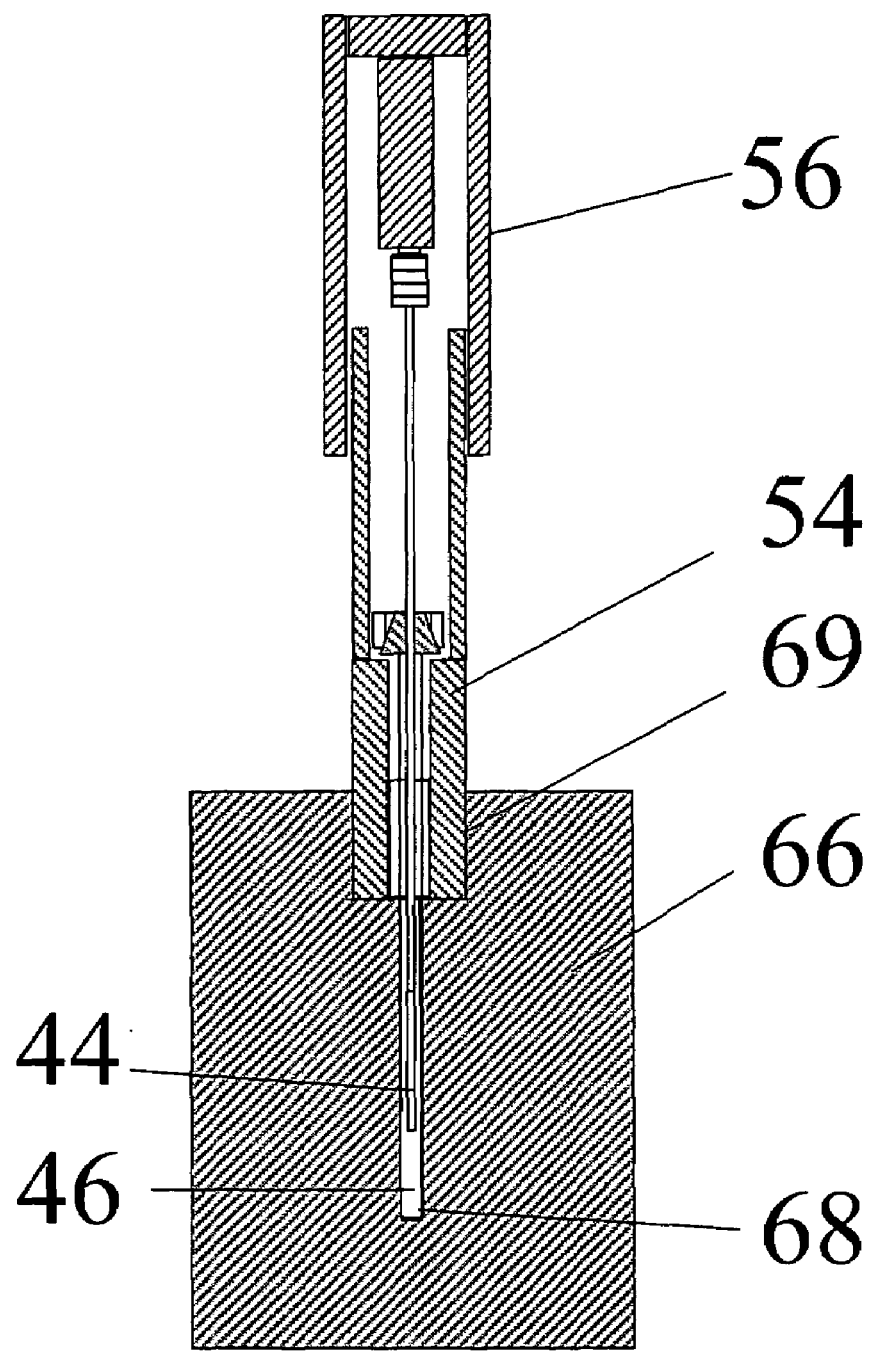
FIG. 15 is a schematic sectional view of a coated fiber in a protective needle placed in an autosampler tray being multiple device holders and having cavities that allow seal of the fiber airtight.

FIGS. 12, 13 and 14 illustrate the on-site operation of the device. FIG. 12 shows the sampling device 50 in an open position. In this position, the open end of the capillary 46 is not sealed. FIG. 13 shows that by moving plunger 56 down, the end of the fiber with a coating 44 is exposed to the fluid carrier via openings 62. The position of the sampling device 50 showed on FIG. 13 allows fast extraction. Alternatively, as illustrated on FIG. 14, by moving plunger 56 up to a predetermined position, places the extraction phase coating 44 of the fiber 42 at a fixed distance from the end of the needle 46. The fluid carrier has contact with the open end of the capillary via windows 62. The components in the fluid carrier are extracted after diffusion through the needle 46 by the coating 44. The position of the sampling device 50 illustrated in FIG. 14 allows passive time weighted average sampling. Location of the coating within the needle defines the diffusion length. After the sampling is completed, the open end of the capillary can be sealed using the sealing element 58 placed in a closed position, as shown in FIG. 11, to prevent loss of extracted components from the extraction phase coating. After the device has been transported to the laboratory it can be placed in an autosampler tray for automated determination of extracted components. FIG. 15 shows the sampling device, with the sealing element removed and placed in an opening 69 of an autosampler tray 66, having cavity 68 which seals the open end of the capillary 46 airtight. This is required to prevent loss of analytes from the coating 44 during quantification. It is anticipated that autosampler tray will be equipped to handle multiple devices and can be designed to match 96 well plate design. Movement of the sampling device from the autosampler tray to the inlet of a suitable analysis instrument by the autosampler arm can be accomplished by using magnetic components or locking mechanisms in the plunger 56 or other means. In some applications the autosampler tray 66 can also be carried to the sampling site together with number of sealed needles instead of transporting individual devices.

Figure 16:
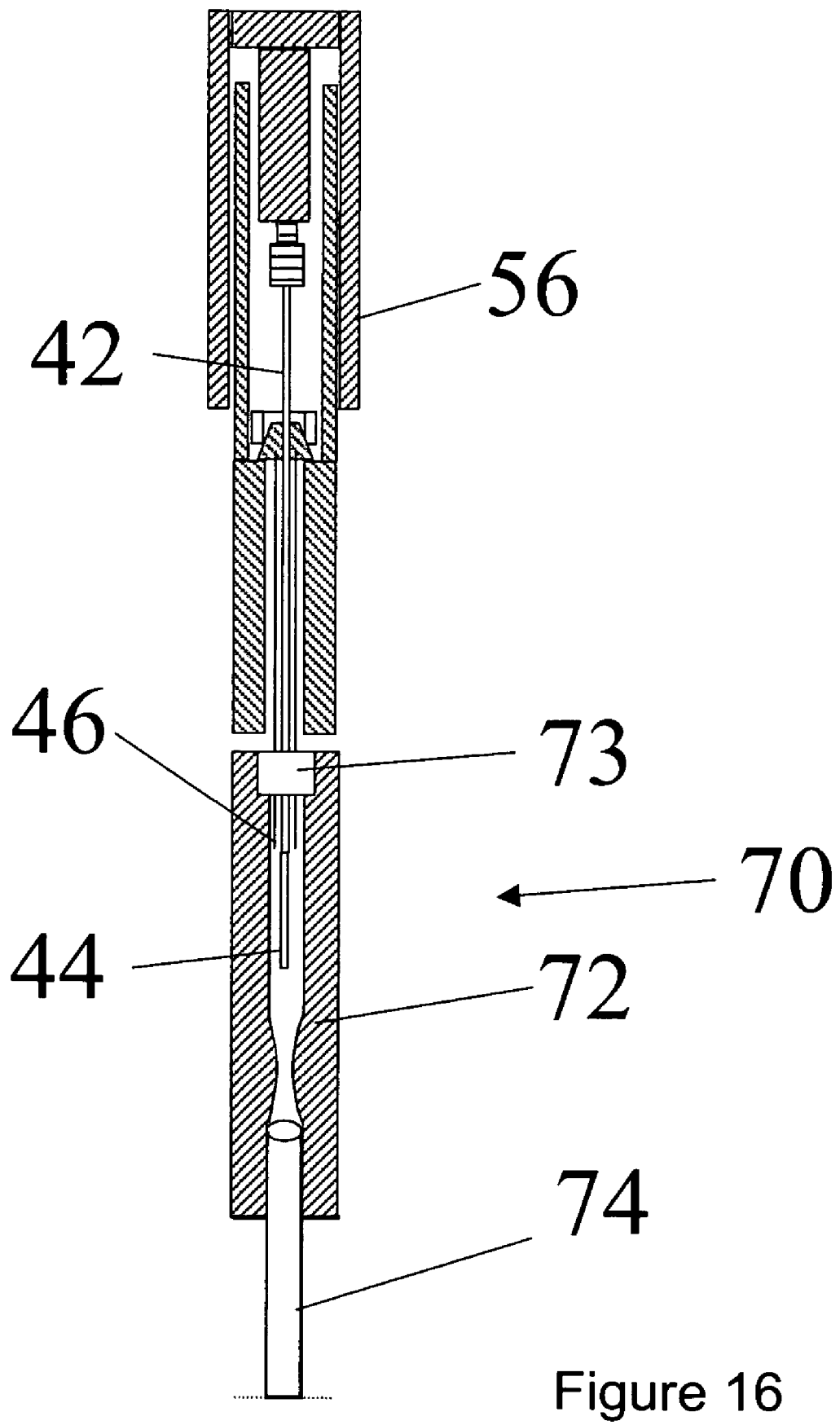
FIG. 16 is a schematic sectional view of a tubular member and a coated fiber in an inlet system to analytical instrument.
Figure 17:
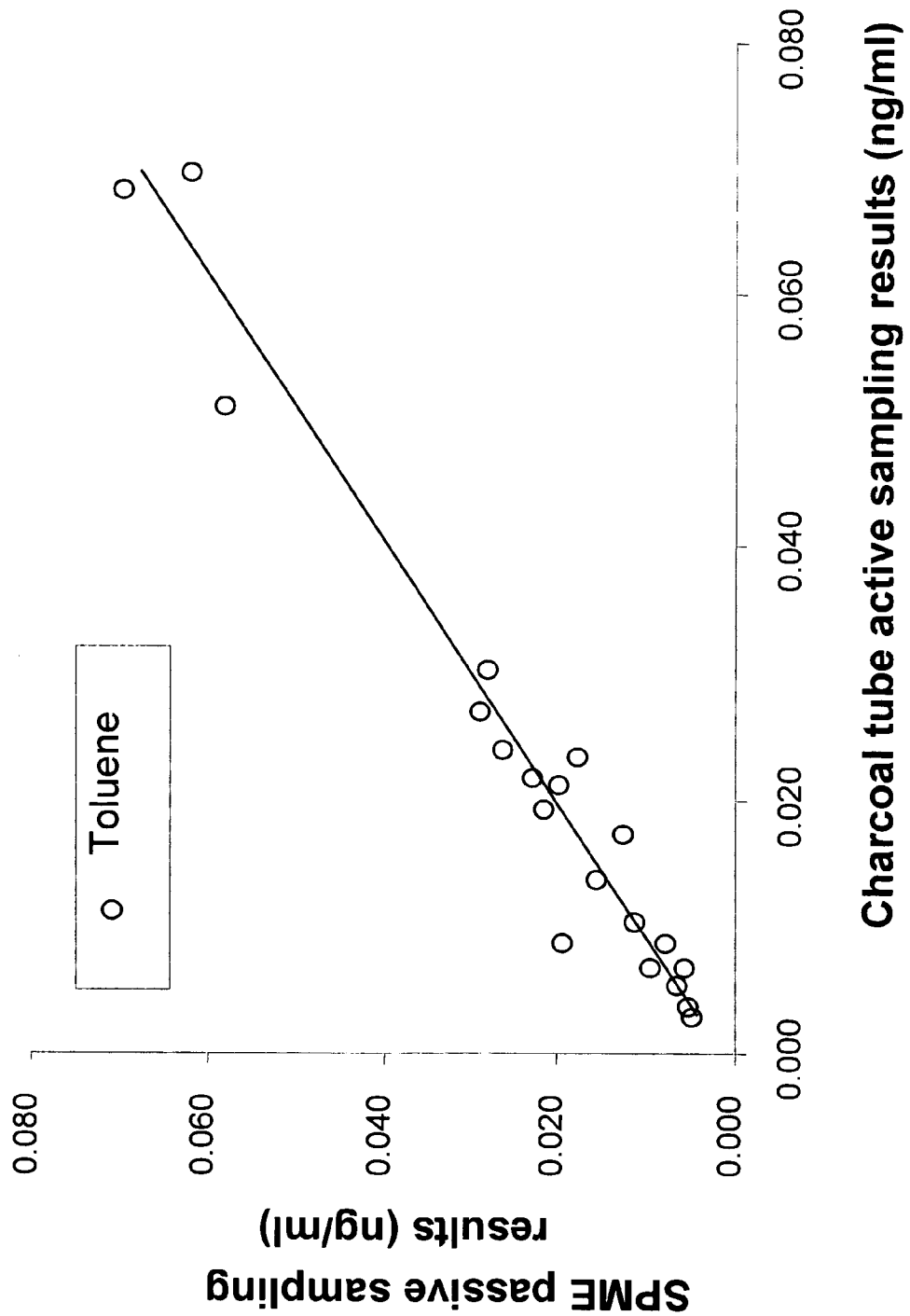
FIG. 17 is a graph showing field time weighted average (TWA) sampling Toluene data obtained with the device illustrated in FIG. 14 and compared with data obtained for standard technique.

FIG. 16 shows the sampling device in the inlet 72 to the analysis instrument (not shown). The capillary 46 penetrating through the septa 73 into the liner 46 and the end of the fiber 42 containing coating 44 is exposed to the desorption fluid (not shown) from the capillary 46 by lowering position of the plunger 56. The desorption of the extracted analytes are facilitated by high linear flowrates of the desorption fluid and high temperatures in the inlet. The desorbed components are transferred to the detection device for determination via a transfer line or chromatographic column 74. FIG. 17 illustrates validation data of the passive time weighted average sampling and obtained using device 50 in the arrangement showed on FIG. 14 compared to standard active time weighted average sampling obtained by using charcoal tubes and pumps. The data show an excellent agreement between results obtained by the sampling device 50 and the standard devices, with the advantage of being less expensive, easier to operate and solventless.

Figure 18:
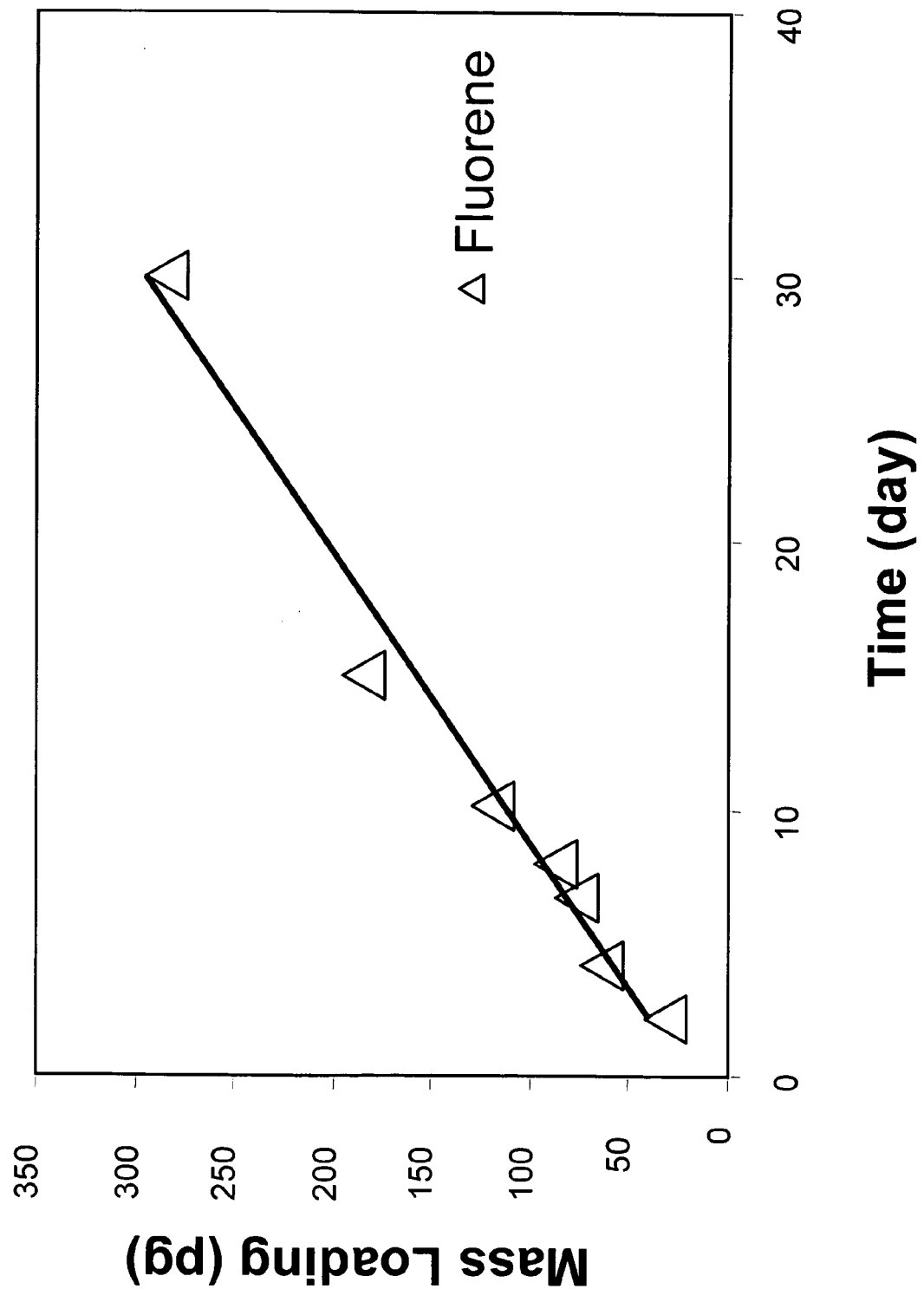
FIG. 18 is a graph showing linear accumulation of Fluorene from water by the coating as a function of time using devices illustrated in FIGS. 10 and 14.

FIG. 18 was obtained for the time weighted average sampling of aqueous samples using the tubular member construction illustrated on FIG. 10 incorporated in the housing 51 in a position showed on FIG. 14. Additional operation is required when directly sampling liquid samples which involves drawing the appropriate liquid into the needle prior to time weighted average (TWA) sampling, and removal of the liquid after the sampling. FIG. 18 illustrates the linear increase in Fluorene accumulated by the coating from spiked aqueous sample using the sampling device 50 with the tubular member 40 and in position showed on FIG. 13. These data demonstrate the suitability of this device for TWA sampling in water.

Figure 19:
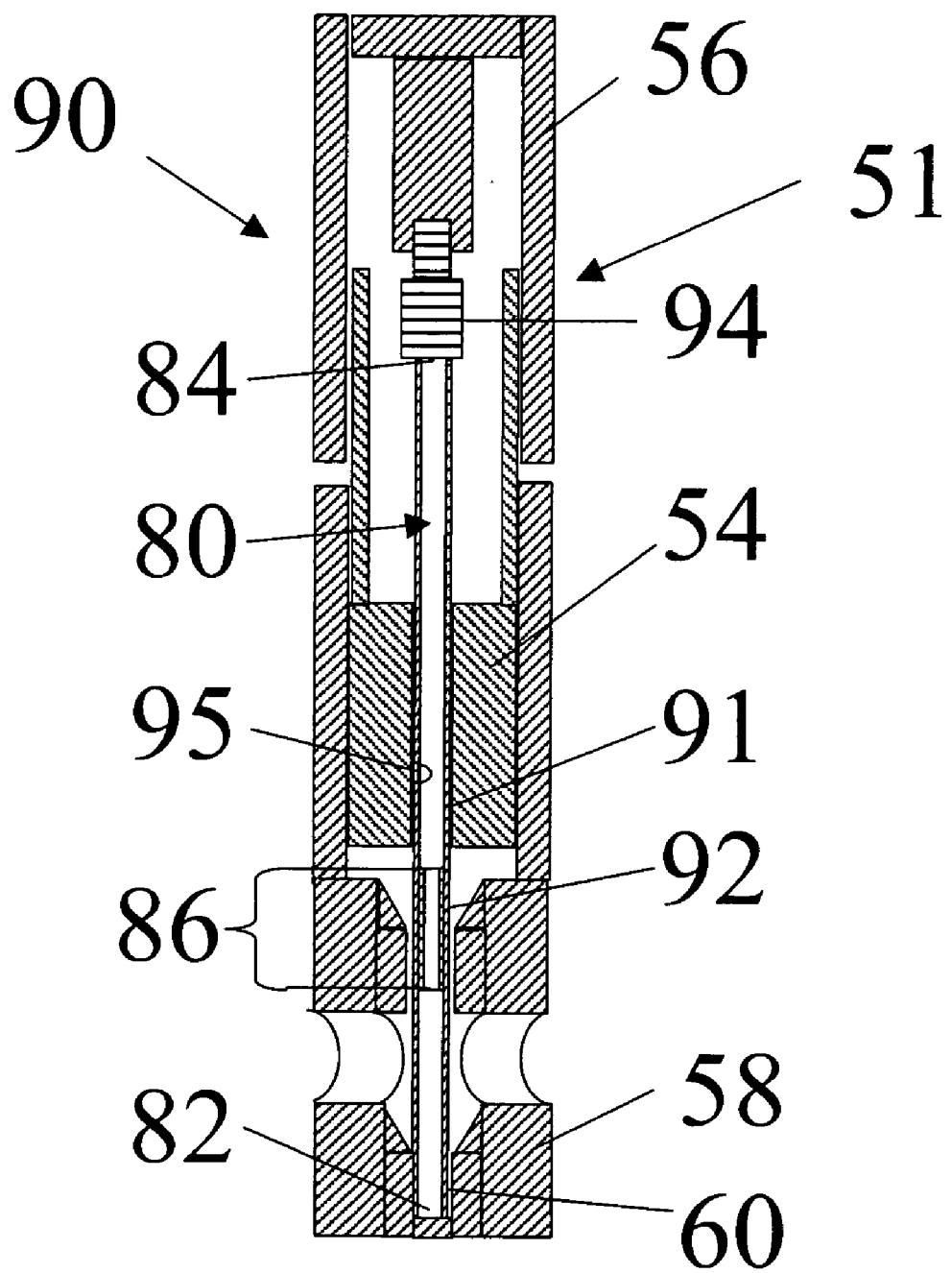
FIG. 19 is a schematic sectional view of tubular member consisting of internally coated hollow fiber (capillary) with a side hole in its wall airtight sealed in a protective housing.

FIG. 19 shows another preferred design 90 of the solid phase microextraction device. In this embodiment tubular member 80 is a capillary 91. The capillary 91 is made of any hard material including plastic material, metal, deactivated stainless steel, alloy or fused silica. The capillary 91 can be a needle. Tubular member 80 has an open end 82 and a closed end 82. Near the open end 82 of the capillary 91 is a zone 86 of a capillary with an extraction phase coating 92 located on the inner surface of the capillary. The zone 86 could be located at any position of the capillary, but is preferably located near the open end 82 of the capillary 91. Also, the material from which the capillary 91 is formed could be made of a material that would provide an extracting surface without the use of a coating. Capillary 91 is sealed at the closed end 84 with a screw fitting 94. There is a side hole 95 in a wall of capillary 91 located in-between the zone 86 and sealed end 84. The housing 51 consisting of sealing element 58, supporting element 54 and plunger 56 is used to operate the tubular member 80 consisting of capillary 91 in a similar way as tubular member 40 consisting of fiber 42 in capillary 46 (FIG. 11). The capillary 91 contains coating 92 at a predetermined distance from the open end 82, which determines the diffusion distance in a time average sampling operation. The other end of the hollow fiber is sealed permanently with screw fitting 94, which attaches to the plunger 56. The supporting element 54 seals the side hole 95 in the capillary 91, but can slide along the capillary freely to provide open position for the side hole 95. In the closed position, cavity 60 in a sealing element 58 seals the open end of the capillary airtight.

Figure 20:
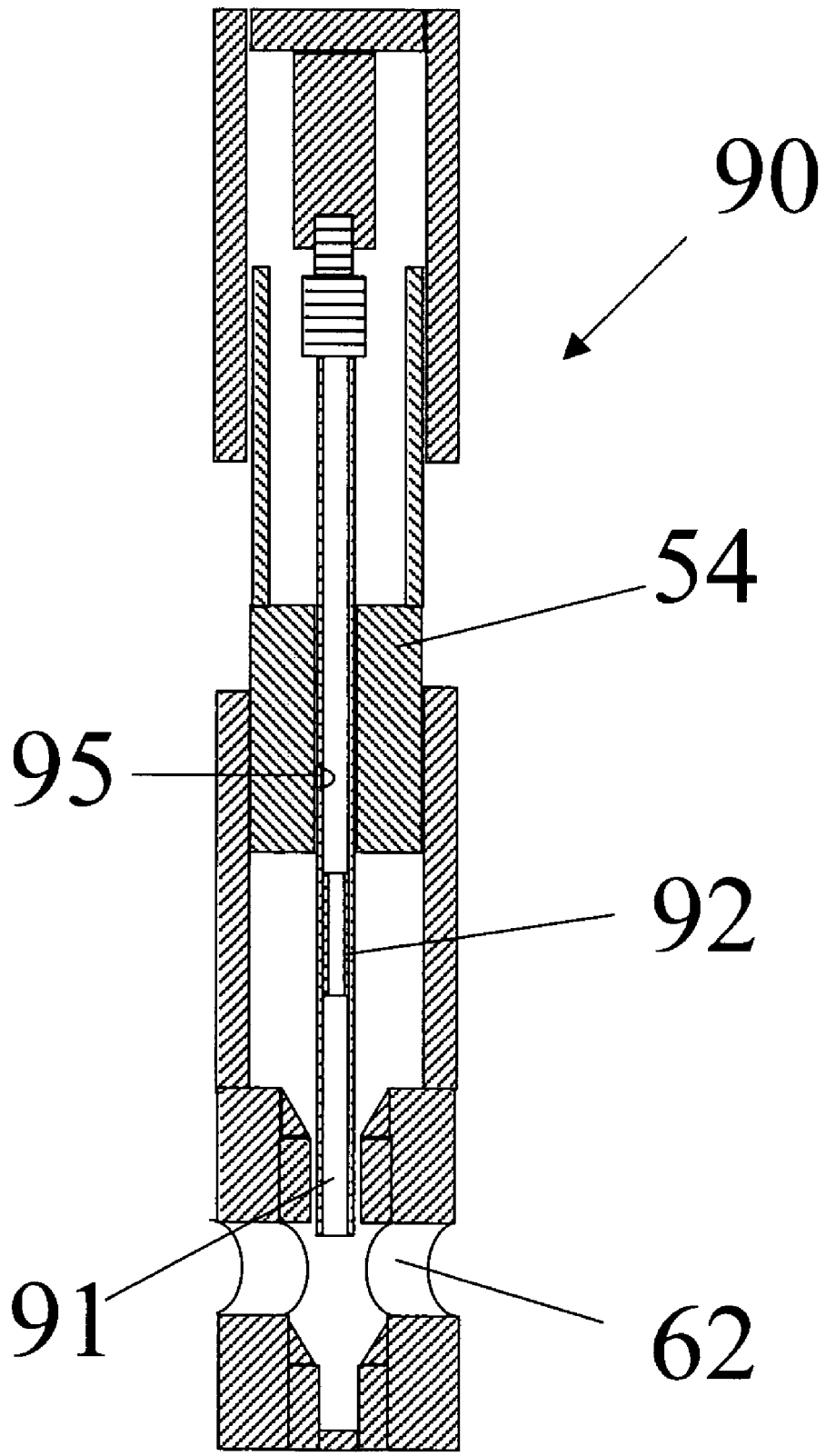
FIG. 20 is a schematic sectional view of internally coated capillary (needle) with a side hole in open position in a protective housing.
Figure 21:
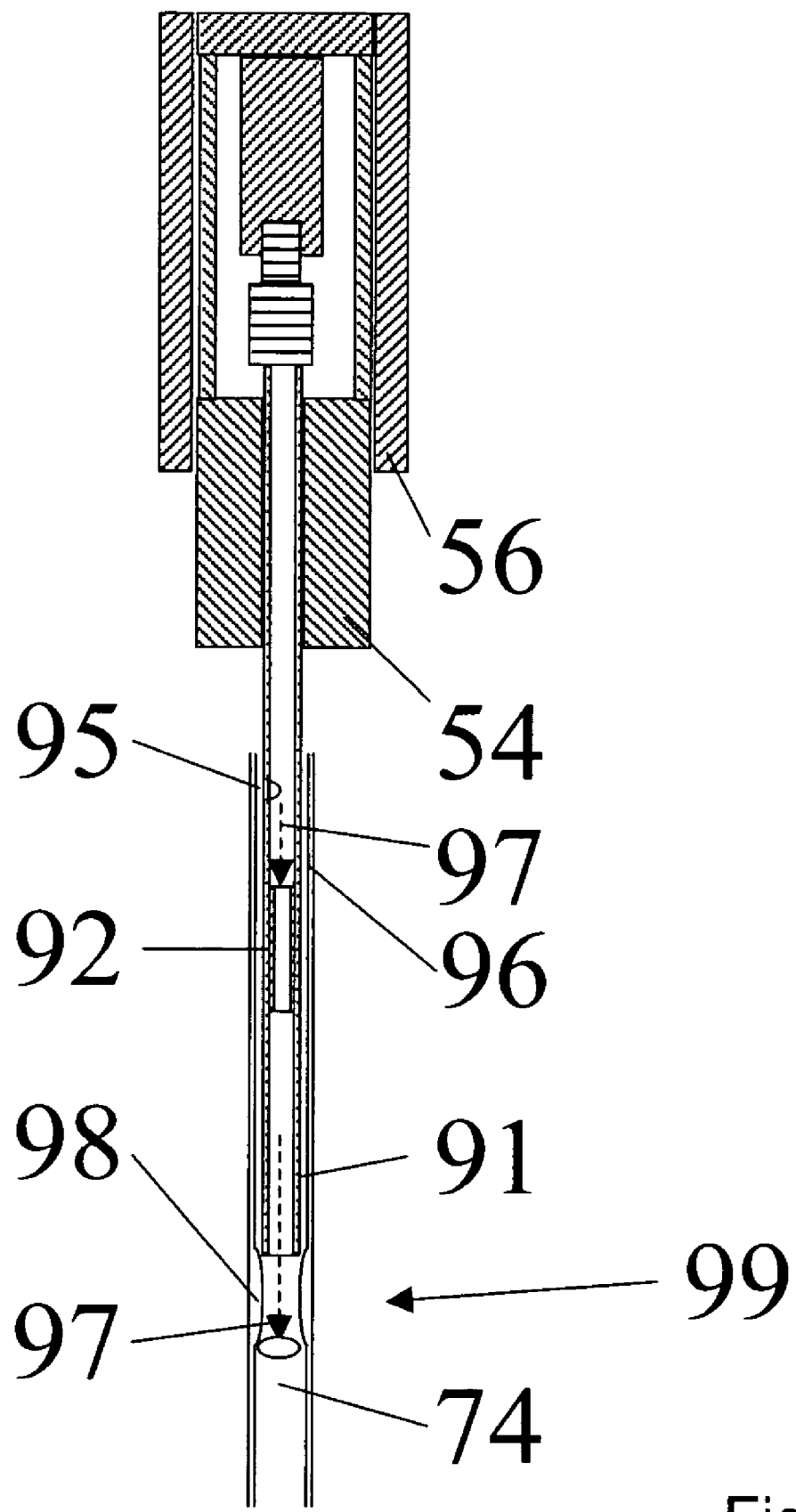
FIG. 21 is a schematic sectional view of internally coated capillary a side hole in an inlet system to analysis instrument.
Figure 22:
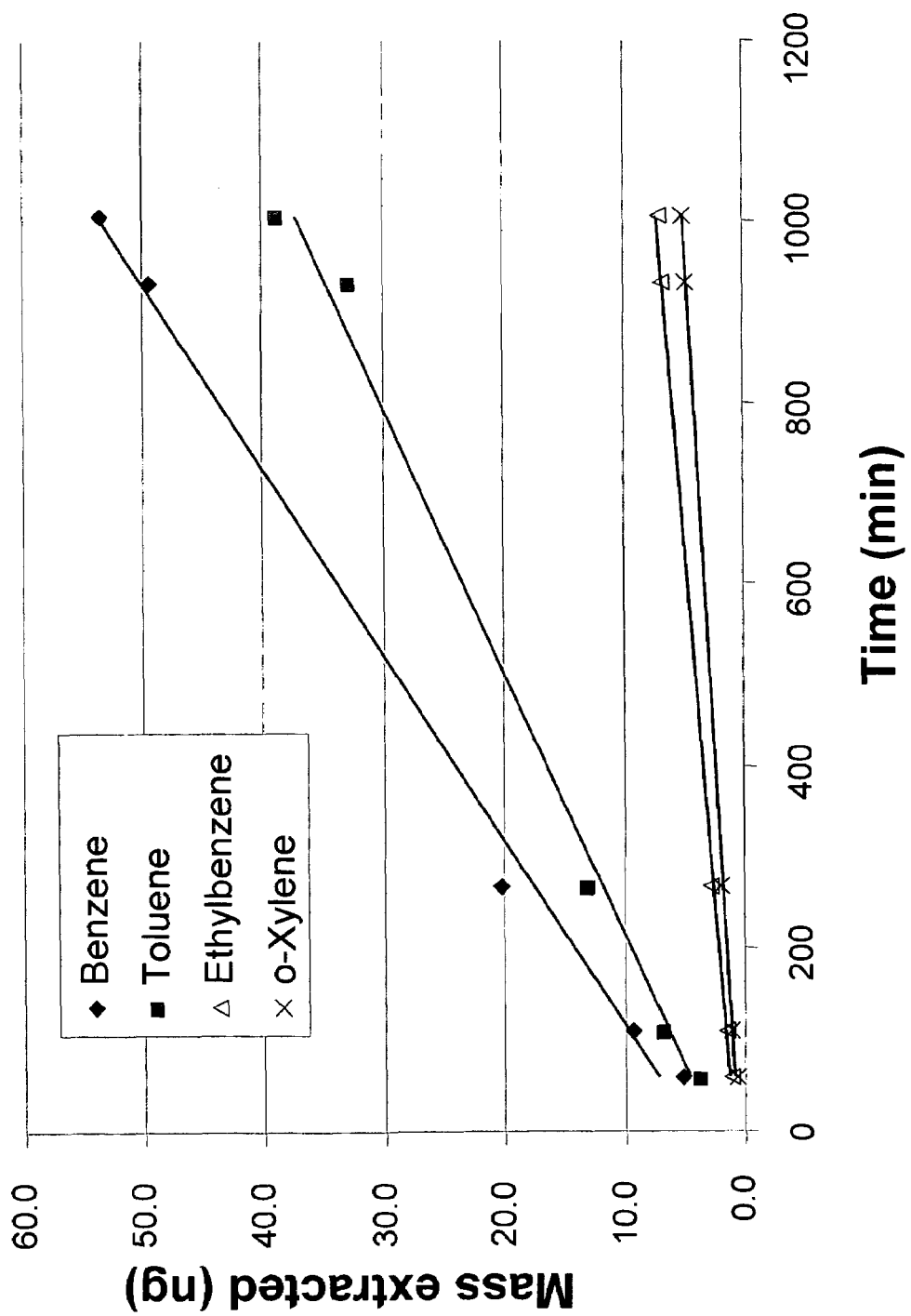
FIG. 22 is a graph showing linear accumulation of Benzene, Toluene, Etylbenzene and Xylene from standard gas mixture onto the coating as a function of time using device illustrated on FIG. 20.

FIG. 20 shows the sampling device 90 in an open position ready for sampling, when the cavity 60 is in open position. The fluid carrier can access the open end of the capillary 91 through openings 62 in sealing element 58. Components in the fluid carrier diffuse through the capillary 91 to reach the coating 92. After sampling is completed, the open end of the capillary 91 is sealed in the cavity 60 of the sealing element 58 and transported for analysis to laboratory. Prior to the determination of extracted components, the sealing element 58 is removed and the capillary 91 is introduced into the inlet to a suitable analysis instrument. FIG. 21 shows the capillary 91 with the coating 92 in the liner 96 of the inlet 99. During the desorption, the supporting element 54 slides towards the plunger 56 along capillary 91 and exposes the side hole 95. The liner 96 has a narrow neck 98 which facilitate sealing of the open end of the capillary 91 and therefore forces the desorption fluid to enter the capillary through the side hole 95 and pass through the capillary 91. Arrows 97 indicate the direction of the desorption fluid flow. The high linear flow of the desorption fluid in the narrow capillary 91 facilitates rapid removal of the analyte from the coating to the transfer line or chromatographic column 74. High temperatures can be used to further accelerate desorption. Alternatively, automated analysis can be performed by using appropriate autosampler trays having cavities similar in design to that showed in FIG. 15 and described above. FIG. 22 shows the linear accumulation with time of Benzene, Toluene, Ethylbenzene and Xylene from standard gas mixture on the coating using device 90 in a position showed in FIG. 20. This behavior demonstrates suitability of this sampling device in time weighted average sampling.

The application of sampling devices showed on FIGS. 11 and 19 are very convenient for on-site field operation, where use of exposed needles might be hazardous. The housing 51 converts the capillaries (needles) convenient to handle structures similar in shapes to pen or sticks.

In addition to the analyte concentration measurement at a well defined place in space and time, a time weighted average (TWA) sampling is possible with the simple SPME devices 50 and 90 (FIGS. 11 and 19). This is particularly important in field measurements when changes of analyte concentration over time, and place to place variations, must often be taken into account.

When the extracting phase is not exposed directly to the sample, but is contained in the tubular member or needle without any flow of the sample through it, the extraction occurs through the static gas phase present in the tubular member. The integrating system can consist of an extracting phase coating on the interior of the tubing as shown in FIG. 3 or 19, or it can be an externally coated fiber withdrawn into the needle as shown in FIGS. 1, 2 and 11. These geometric arrangements represent a very powerful method able to generate a response proportional to the integral of the analyte concentration over time and space (when the tubing or needle is moved through the space). In these cases, the only mechanism of analyte transport to the extracting phase is diffusion through the gaseous phase contained in the tubing. During this process, a linear concentration profile is established in the tubing between the small needle opening, characterized by surface area A and the position of the extracting phase, located at the distance Z from the opening. The amount of analyte extracted, dn, during time interval, dt, can be calculated by considering the first Fick's law of diffusion:

$$dn = AD_g \frac{dc}{dz} dt = AD_g \frac{\Delta C(t)}{Z} dt \qquad (5)$$

where $\Delta C(t)/Z$ is a value of the gradient established in the needle between needle opening and the position of the extracting phase, Z; $\Delta C(t) = C(t) - C_z$, where $C(t)$ is a time dependent concentration of analyte in the sample in the vicinity of the needle opening, and $C_z$ concentration of the analyte in the gas phase in the vicinity of the coating $C_z$ is close to zero for a high coating/gas distribution constant capacity, then: $\Delta C(t) = C(t)$. The concentration of analyte at the coating position in the needle, $C_z$, will increase with integration time, but it will be kept low compared to the sample concentration in the sample $C(t)$ because of the presence of the sorbing coating. Therefore the accumulated amount over time can be calculated as:

$$n = D_g \frac{A}{Z} \int C(t) dt \qquad (6)$$

As expected, the extracted amount of analyte is proportional to the integral of a sample concentration over time, the diffusion coefficient of analytes in gaseous phase, $D_g$, area of the needle opening, A, and inversely proportional to the distance of the coating position in respect of the needle opening, Z. It should be emphasized that equation 5 is valid only in a situation where the amount of analyte extracted onto the sorbent is a small fraction (below RSD of the measurement, typically 5%) of equilibrium amount in respect to the lowest concentration in the sample. To extend integration times, the coating can be placed deeper into the needle (larger Z), the opening of the needle can be reduced by placing an additional orifice (smaller A), or a high capacity sorbent can be used. The first two solutions will result in a low measurement sensitivity. An increase of sorbent capacity presents a more attractive opportunity. It can be achieved by either increasing the volume of the coating, or its affinity towards the analyte. An increase of the coating volume will require an increase of the device size. The optimum approach to increased integration time, is to use sorbents characterized by large coating/gas distribution constants.

While air will be the usual atmosphere within the tubular member, obviously, other atmospheres can be utilized in the same manner as described with respect to air. In case of sampling liquids the tubular member showed on FIG. 10 can be used to fill the interior of the tubular member with appropriate liquid prior sampling. The solid phase microextraction device described in this application facilitate the ultimate goal of chemist to perform analysis on-site at place where a sample is located rather than moving the sample to laboratory, as it is a common practice in many cases at present. This approach eliminates errors and reduces the time associated with sample transport and storage and, therefore, it results in more accurate, precise and faster analytical data.

The device and method of the present invention can also be used for extraction and analysis of gases and for supercritical fluids as well. The method is not limited to analysis of organic analytes but also for inorganic ions by using ion-exchange materials located on the fiber surface. In addition to thermal desorption by direct heating, laser desorption or conductive heating, for example, microwave desorption or Curie point magnetic hysteresis method could be used. Both solid fibers and hollow fibers, or other tubular members, will be suitable depending on the use that is being made of the present invention. For example, fused silica, graphite fibers, fibers constructed with solid polymeric materials and even metal and metal wires can be used as fibers and the fibers can be coated with various materials or uncoated. Some suggested coatings are CARBOWAX (a trade mark), poly(dimethylciloxane), poly(divilylbenzene), poly(divinyldibenzene), carbon, NAFION (a trade mark), nylon, octadecyltrichlorosilane, polymethylvinylchlorosilane, liquid crystalline polyacrylates, silicone, polyimide, grafted self-assembled monolayers, polypyrrole, monolithic sorbents derived from a sol-gel process, immobilized antibodies, gold and other inorganic coatings. Fibers coated with these coatings are stored under pure nitrogen or helium or sealed in appropriate housings illustrated on FIG. 11, 15 or 19 to prevent absorption of the volatile organics present in air. The coatings can be organic or inorganic, for example, fused silica surface.

In addition to having coating located on an outer surface of a solid fiber, coating could be located on an inner surface of a capillary or other tubular member. Coating could also be located on the packing material used with the fiber. In addition to direct extraction, the method of the present application could be performed with prior activation using organic solvents by using the optional inlet 26 on the syringe. The analytical instrument used with the method of the present invention can also be varied. For example, a gas chromatograph, a liquid chromatograph or a supercritical fluid chromatograph could be used. Other analytical methods such as flow injection analysis, mass spectrometry, atomic absorption or emission including inductively coupled plasma technique could be used.

In addition to analyzing for environmental contaminants, the method and device of the present invention can be used to monitor or measure the components in industrial process streams. The present invention can also be used to study properties of coatings, for example, absorption, deterioration rates and diffusion coefficients.

Numerous other variations, within the scope of the attached claims, will be readily apparent to those skilled in the art.

I claim:

1. A device for carrying out solid phase microextraction of components contained in a fluid carrier, said device comprising; (a) a tubular member having one closed end and one open end, a zone within said tubular member having an extracting surface; (b) said tubular member being located within a housing, said housing having movable sealing element, said sealing element having a fixed cavity structure at a set position within said sealing element to which said open end of said tubular member fits forming an airtight seal, said sealing element being movable, said cavity providing an open position and a closed position for said tubular member, said cavity sealing said open end when said cavity is in said closed position and permitting contact between said fluid carrier and said open end when in said open position; (c) said movable sealing element having openings permitting contact between said fluid carrier and said open end of said tubular member when in said open position; (d) said tubular member being sized and shaped to fit into an injection port of a suitable analysis instrument where said components can be desorbed from said extracting surface.

2. A device as claimed in claim 1 wherein there are means to fill the tubular member with the fluid earner.

3. A device as claimed in claim 1 wherein said tubular member is designed such that when placed into said injection port a desorption fluid can flow through said tubular member into said port to assist in desorption.

4. A device as claimed in claim 1 wherein an extracting surface of said zone is formed by an extracting phase coating on a surface of said tubular member within said zone.

5. A device as claimed in claim 4 wherein said zone extends along a length of said tubular member.

6. A device as claimed in claim 4 wherein said zone is located near said open end.

7. A device as claimed in claim 4 wherein said coating is formed of a material selected from the group of non-polar and polar coatings.

8. A device as claimed in claim 4 wherein the coatings are formed of a material selected from the group of poly(dimethylsiloxane), poly(divinyldibenzene), poly(divinyldibenzene), carbon, monomers with minor amounts of ionomers produced by copolymerization of fluorocarbon appropriate acid or ester, nylon, polyethylene glycol, silicone, polyimide, octadecyltrichlorosilane, polymethylvinylchlorosilane, liquid crystalline polyacrylates, grafted self-assembled monolayers, polypyrrole, monolithic sorbents derived from a sol-gel process, immobilized antibodies, gold and other inorganic coatings.

9. A device as claimed in claim 1 wherein the tubular member comprises a fiber inside a capillary said fiber being movable within said capillary.

10. A device as claimed in claim 9 where said zone of said extraction surface is located at said fiber.

11. A device as claimed in claim 9 where the outside diameter of a portion of said fiber is identical to the inner diameter of said capillary.

12. A device as claimed in claim 1 wherein said tubular member is a capillary.

13. A device as claimed in claim 12 wherein said capillary has a side hole in-between said zone and said closed end.

14. A device as claimed in claim 13 wherein said capillary is surrounded by a movable supporting element, said supporting element providing a sealed position and open position for said side hole, said open position being used during desorption of said components into a suitable analysis instrument.

15. A device as claimed in claim 1 wherein said tubular member is made of hard plastic, metal, deactivated metal, alloy or fused silica.

16. A method of using a device for solid phase microextraction of components from fluid carrier, said device having a tubular member having one closed end and one open end, a zone within said tubular member having an extracting surface, said tubular member being located within a housing, said housing having a movable sealing element, said sealing element having a fixed cavity structure at a set position within said sealing element to which said open end of said tubular member fits forming an airtight seal, said sealing element being movable, said cavity providing an open position and a closed position for said tubular member, said method comprising exposing the device to the fluid carrier, placing the sealing element in said open position permitting contact between said fluid carrier and said open end, placing said sealing element in a closed position, removing said sealing element, inserting said tubular member into an injection port of a suitable analysis instrument and desorbing said components from said extracting surface.

17. A method as claimed in claim 16 where said tubular member is filled with fluid carrier prior to exposing said device to said fluid carrier.

18. A method as claimed in claim 16 where the tubular member is inserted into said injection port in a manner that restriction seals around said open end of said tubular member, thereby forcing the flow of desorption fluid through said tubular member.

19. A method as claimed in claim 16 including the steps of removing said scaling element and placing the tubular member into a sealed housing said housing being a multiple tubular member holder, transporting said housing to a suitable analysis instrument, removing said tubular member from said housing and desorbing components into said instrument.

20. A method as claimed in claim 19 wherein said analytical instrument is automated, said method including the steps of automatically removing a tubular member from said housing being a multiple tubular member holder and placing said tubular member into an inlet to said instrument and automatically carrying out desorption.

* * * * *